US00PP11163P

United States Patent [19]

Hanna

[11] Patent Number: Plant 11,163

[45] Date of Patent: Dec. 21, 1999

[54] BERMUDAGRASS NAMED 'TIFEAGLE'

[75] Inventor: Wayne W. Hanna, Chula, Ga.

[73] Assignee: The United States of America as represented by the Department of Agriculture, Washington, D.C.

[21] Appl. No.: 08/900,007

[22] Filed: Jul. 24, 1997

[51] Int. Cl.[6] ..... A01N 5/00

[52] U.S. Cl. ..... Plt./389

[58] Field of Search ..... Plt./90, 389

*Primary Examiner*—Howard J. Locker
*Assistant Examiner*—Kent L. Bell
*Attorney, Agent, or Firm*—M. Howard Silverstein; C. Andrew Watkins; John D. Fado

[57] ABSTRACT

'TifEagle' is a dense fine-textured triploid (2n=3x=27 chromosomes) bermudagrass which has use on golf greens and other areas requiring mowing heights at 6 mm or less. The grass produces more shoots per unit area that are shorter with narrower and shorter leaves than 'Tifdwarf', the previous cultivar of choice for high quality putting greens mowed at 6 mm or less on golf courses where burmudagrass is preferred. 'TifEagle' consistently produced better quality turf and color than 'Tifdwarf' at mowing heights less than 6 mm. It shows more resistance than 'Tifdwarf' to the tawny mole cricket after one year of establishment.

3 Drawing Sheets

BACKGROUND OF THE NEW VARIETY

Burmudagrass, Cynodon spp. (L) Pers is a warm-season, perennial, sod-forming grass that spreads by stolons and rhizomes. Bermudagrass probably originated from Africa and South and Southeast Asia but it has been introduced to all tropical and subtropical regions of the world.

The genus has been observed to survive at 50° N. in Europe and to 4000 m elevation in the Himalayas. It is also found in the Pacific, Atlantic and Indian Oceans.

Roots and rhizomes of this genus can penetrate the soil to a depth of 1 m or more. A large amount of morphological variation exists in this species.

Both common and triploid hybrid types are used for turf. Common types have 2n=18 or 36 chromosomes and usually produce seeds. Triploid hybrids have 2n=3=27 chromosomes and are male and female sterile. Both can be propagated by stolons and/or rhizomes. Only common burmudagrass types can be propagated by seeds.

Burmadagrass can be used to produce an attractive wear-resistant turf if managed properly. 'Tifway II° (unpatented) is a medium fine 2n=3x=27 chromosome cultivar induced in 'Tifway' (unpatented) with 9,000 rads of gamma radiation of dormant stolons and released by the USDA-ARS and the University of Georgia Coastal Plain Experiment Station in 1981 for use in USDA plant hardiness zones 8 and higher (USDA Agricultural Handbook 170). 'Tifway II' has good pest resistance and wear tolerance. 'Tifdwarf' (unpatented) is a fine 2n=3x=27 chromosome cultivar selected on a small patch about 460 mm in diameter growing on a golf green at the Country Club, Florence, S.C. It was evaluated and released by the USDA-ARS and the University of Georgia Coastal Plain Experiment Station in 1965 for use in USDA plant hardiness zone 8 and higher (USDA Agricultural Handbook 170). 'Tifdwarf' is the cultivar of choice for high quality putting greens mowed at 6 mm or less on golf courses where bermudagrass is preferred (in general, 32° north and south of the equator).

Although 'Tifdwarf' is mowed down to 3 mm height on some golf courses for short periods of time, the density of the turf rapidly becomes thin contributing to weed and algae problems. There is an increased emphasis each year to mow bermudagrass greens at 3 mm for longer periods of time to produce faster ball roll on the greens. A burmudagrass is needed that will maintain good turf quality (affected by density) when mowed at 3 mm for long periods of time.

Mutagens have been used to induce dwarfness in numerous croops. An induced fine-textured mutant in 'Tifway II' will combine good pest resistance, wear tolerance and high turf quality in another genotype.

SUMMARY OF THE INVENTION

'TifEagle' is a dense, fine-textured triploid (2n=3x=27 chromosomes) bermudagrass which has use on golf greens and other areas requiring mowing heights at 6 mm or less. The grass produces more shoots per unit area that are shorter with narrower and shorter leaves than 'Tifdwarf'. It consistently produced better quality turf and color than 'Tifdwarf' at mowing heights less than 6 mm. It shows more resistance than 'Tifdwarf' to the tawny mole cricket after the grass was established for one year.

DETAILED DESCRIPTION OF THE PLANT

Figure 1:
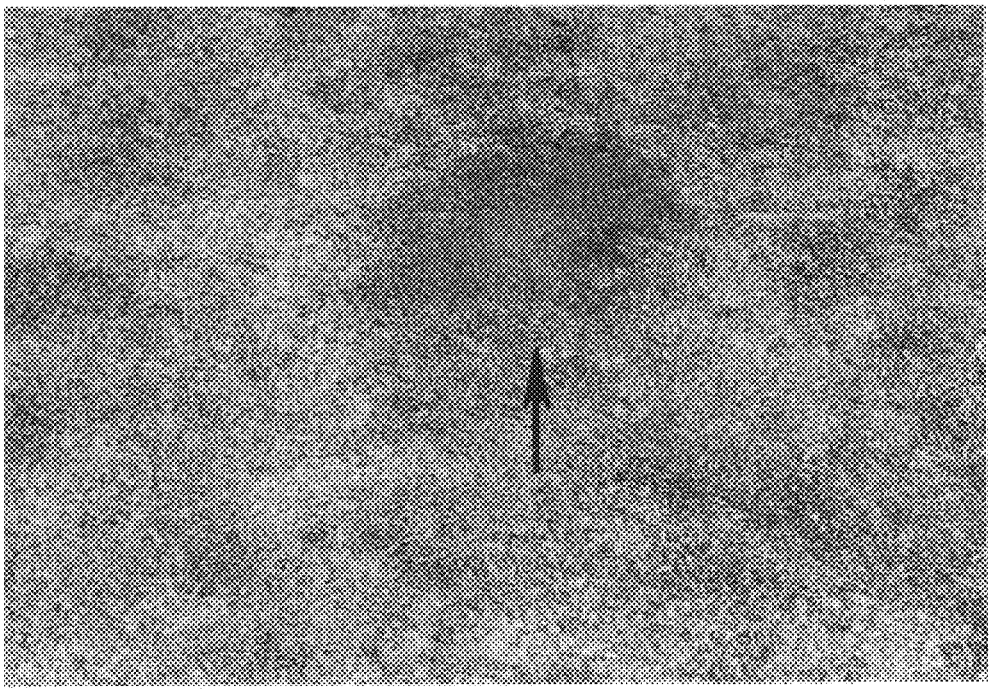
FIG. 1 is a photograph of 'TifEagle' as it was originally found in 1990 as a dense offtype (arrow) in a plot of Mutant number 2 that was derived from irradiated dormant stolons of 'Tifway 2' and mowed at 6 mm beginning in the spring of 1989.
Figure 2:
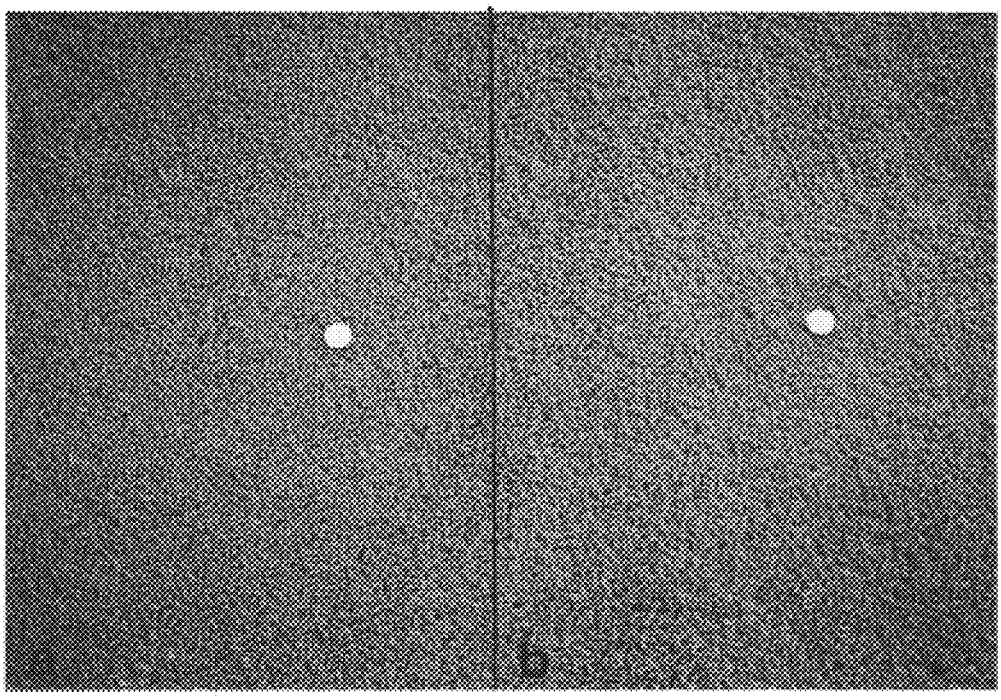
FIG. 2 is a photograph of 'TifEagle' (a) and 'Tifdwarf' (b) mowed at 6 mm height showing the finer texture and more dense growth of 'TifEagle' compared to 'Tifdwarf'.
Figure 3:
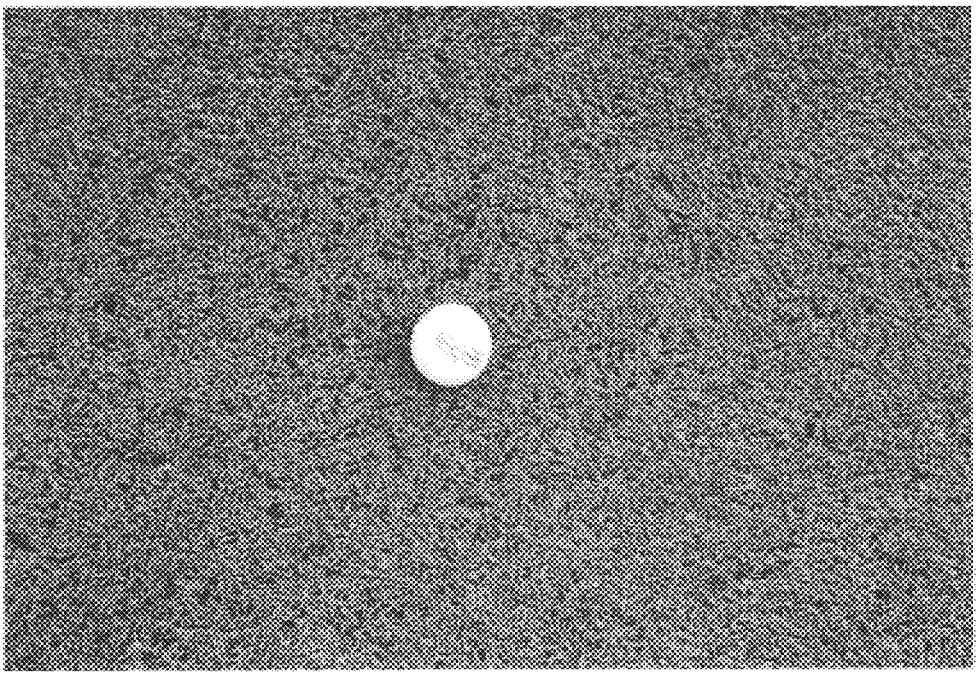
FIG. 3 is a photograph of 'Tifdwarf' mowed at 3 mm height showing the open plant canopy and growth of algae (dark areas).
Figure 4:
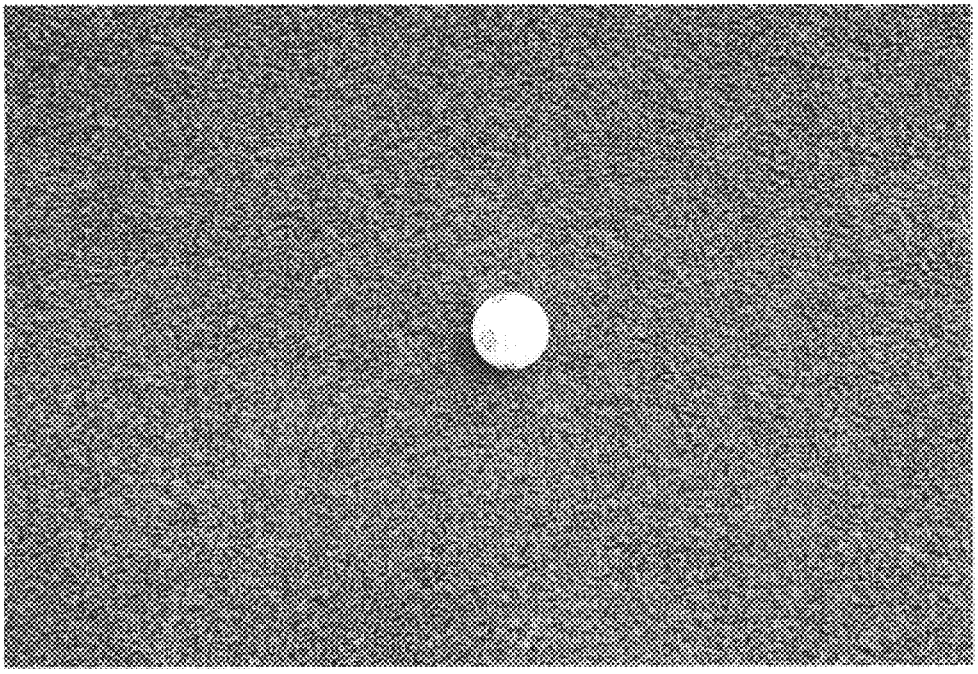
FIG. 4 is a photograph of 'TifEagle' mowed at 3 mm height (growing adjacent to 'Tifdwarf' in FIG. 3) showing dense plant canopy and high-quality turf.
Figure 5:
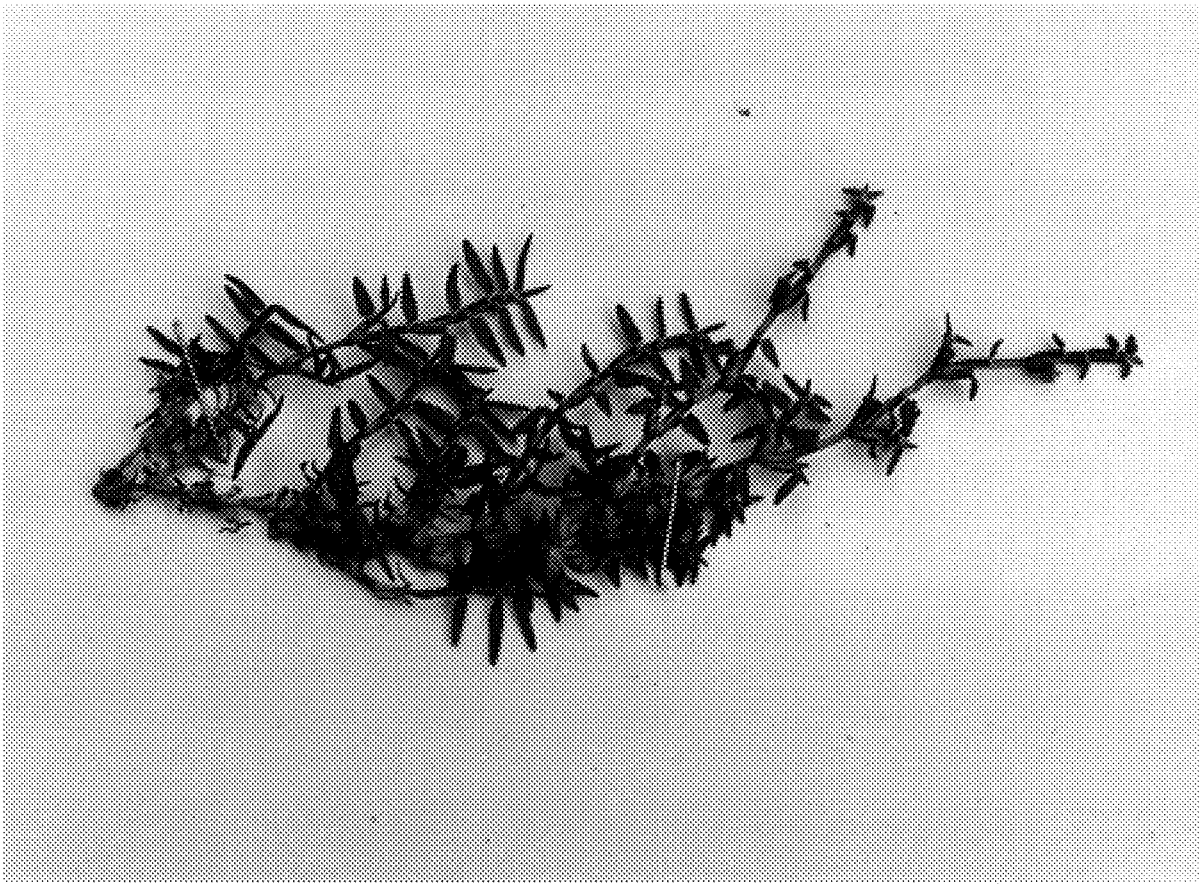
FIG. 5 is a photograph of a typical stolon of 'TifEagle'.

Bermudagrass 'TifEagle' is a fine-textured mutant selected from plants established from dormant stolons of the 'Tifway II' cultivar of *Cynodon dactylon* (L.) Pers.×*C. transvaalensis* Butt-Davy treated with 7000 rads of Cobalt 60 gamma radiation on Jan. 12, 1988. Dormant stolons of 'Tifway II' were obtained from a plot maintained by Dr. G. W. Burton at the Coastal Plain Experiment Station, Tifton, Ga. Raddiation treated stolons were planted in steam-sterilized soil in flats in the greenhouse at Tifton, Ga. immediately after treatment. Forty-eight putative fine-textured mutants were selected, but only 45 of the putative mutants survived and were individually propagated. On Jul. 11, 1988, these putative mutants were planted in the center of 1.8 mm×2.6 m plots and allowed to spread and cover the plots. Beginning in April, 1989, and continuing through the growing season in 1990, the plots were mowed at 6 mm three times per week. In July 1990, a dense fine-textured off-type grass that did well at 6 mm mowing height was observed in putative mutant number 2 which was originally selected as a fine-textured off-type. The dense off-type mutant was vegetatively increased, tested as TW 72 and later named 'TifEagle'. 'TifEagle' has been tested in Tifton, Ga.; Savannah, Ga.; Ft. Lauderdale, Fla.; West Palm Beach, Fla.; Hobe Sound, Fla.; Pinehurst, N.C.; and Memphis, Tenn.

'TifEagle' has 2n=3x=27 chromosomes like 'Tifway II' and 'Tifdwarf' but is morphologically more similar to 'Tifdwarf' than to 'Tifway II'. It has been asexually reproduced by vegetative propagation of shoots, stolon, or rhizomes through plugging, sprigging and sodding. 'TifEagle' is a single genotype that produces a uniform turf. It has been propagated true-to-type from 1990 to 1997.

'TifEagle' has been evaluated in 11 experiments at eight locations (including six golf courses). For comparison to standardized measures, we generally use the 1 to 9 rating system adopted and used by the National Turfgrass Evaluation Program (NTEP). We use the modified 1 to 5 system when variation for a characteristic is limited at a particular rating date. Specifically:

Quality is an overall rating that considers density, color and pest resistance for the cultivar to produce a desirable putting surface on a golf green. 1=poor and 9=excellent Color is based on The Royal Horticultural Society Colour Charts (1966). Specifically for this cultivar:

| For 1 to 9 rating scale: | For 1 to 5 rating scale: |
|---|---|
| 9 = RHS 137A | 5 = RHS 137A |
| 8 = RHS 137B | 4 = RHS 137C |
| 7 = RHS 137C | 3 = RHS 146C |
| 6 = RHS 146B | 2 = RHS 145B |
| 5 = RHS 146C | 1 = RHS 199B |
| 4 = RHS 146D | |
| 3 = RHS 145B | |
| 2 = RHS 145C | |
| 1 = RHS 199B | |

Greenup is the percent of plot area with green leaves. Specifically:

| For 1 to 9 rating scale: | For 1 to 5 rating scale: |
|---|---|
| 9 = greater than 90% | 5 = greater than 80% |
| 8 = 80 to 89% | 4 = 60 to 79% |
| 7 = 70 to 79% | 3 = 40 to 59% |
| 6 = 60 to 79% | 2 = 1 to 39% |
| 5 = 50 to 59% | 1 = 0% |
| 4 = 40 to 49% | |
| 3 = 20 to 39% | |
| 2 = 1 to 19% | |
| 1 = 0% | |

Density is the percent of ground surface covered by grass. Specifically:

| For 1 to 9 rating scale: | |
|---|---|
| 9 = greater than 90% | 4 = 40 to 49% |
| 8 = 80 to 89% | 3 = 30 to 39% |
| 7 = 70 to 79% | 2 = 20 to 29% |
| 6 = 60 to 79% | 1 = less than 20% |
| 5 = 50 to 59% | |

Seed Heads are the percent of upright shoots with a seed head. Specifically:

| For 1 to 9 rating scale: | |
|---|---|
| 9 = greater than 90% | 4 = 40 to 49% |
| 8 = 80 to 89% | 3 = 20 to 39% |
| 7 = 70 to 79% | 2 = 1 to 19% |
| 6 = 60 to 69% | 1 = 0% |
| 5 = 50 to 59% | |

Mole cricket data estimates the percent of area with mole cricket tunnels. Specifically:

| For 1 to 9 rating scale: | For 1 to 5 rating scale: | For 0 to 5 rating scale: |
|---|---|---|
| 9 = greater than 90% | 5 = greater than 80% | 5 = greater than 80% |
| 8 = 80 to 89% | 4 = 60 to 79% | 4 = 60 to 79% |
| 7 = 70 to 79% | 3 = 40 to 59% | 3 = 40 to 59% |
| 6 = 60 to 69% | 2 = 1 to 39% | 2 = 20 to 39% |
| 5 = 50 to 59% | 1 = 0% | 1 = 1 to 19% |
| 4 = 40 to 49% | | 0 = 0% |
| 3 = 20 to 39% | | |
| 2 = 1 to 19% | | |
| 1 = 0% | | |

Dollar spot ratings are the percent of leaf area infected with the disease. Specifically:

| For the 1 to 5 rating scale: |
|---|
| 5 = greater than 80% |
| 4 = 50 to 79% |
| 3 = 20 to 49% |
| 2 = 1 to 19% |
| 1 = 0% |

In all experiments, the bermudagrass entries were replicated and analyzed statistically. Significant refers to the P=0.05 probability level.

'TifEagle' produced significantly better quality (8.6 on a scale where 9 is best) turf than 'Tifdwarf' (7.5) in three of four years in a 1991 test and one of two years of each 1994 and 1995 tests when mowed at 6 mm height at Tifton, Ga. In tests at seven locations where experiments were mowed less than 6 mm height, 'TifEagle' always produced significantly better quality turf than 'Tifdwarf'. Turf quality was 8.4 versus 5.1 at 3 mm mowing height, 7.9 versus 5.7 at 4 mm mowing height and 8.5 versus 7.3 at 5 mm mowing height for 'TifEagle' versus 'Tifdwarf', respectively. At mowing heights below 6 mm, 'TifEagle' produced a more dense turf that did not allow algae to grow. Because of these and the other improved characteristics described here, TifEagle performs best at a daily mowing height of 3 mm.

'TifEagle' had a significantly higher stimp meter reading or speed of ball roll (8.2 feet) than 'Tifdwarf' (7.6 feet).

After the year of establishment and in high populations of tawny mole crickets (*Scapteriscus vicinus*), 'TifEagle' showed significantly less damage (3.0 on a scale of 1 to 9 where 1 is no damage) to this insect than 'Tifdwarf' (6.0).

No seed heads have been observed on 'TifEagle' whereas varying numbers have been observed on 'Tifdwarf' in May and June.

At a 3 mm mowing height, 'TifEagle' had significantly better color than 'Tifdwarf'. This is due in large part to more leaves remaining on 'TifEagle', whereas more leaves are removed on 'Tifdwarf' at this mowing height. At a 6 mm mowing height, 'TifEagle' has a subtle lighter green color than 'Tifdwarf' which is noticeable if they are growing side by side. This is probably due to less anthocyanin in leaves of 'TifEagle' than in 'Tifdwarf' and is reflected in less red plant discoloration in 'TifEagle' in the fall in certain years due to cool nights before the plants go dormant.

Thatch is the thickness in millimeters of the dead material above the soil surface.

'TifEagle' produces significantly more thatch (about 25%) than 'Tifdwarf'. The thatch can be controlled with verticutting, topdressing and/or grooming to produce a desirable putting surface.

The fluorescent-labeled AFLP method was used to detect DNA fragments that could be used to distinguish 'TifEagle', 'Tifway II', 'Tifdwarf' and 'FHB-135' (U.S. Plant Pat. No. 9,030) now being marketed as 'FloraDwarf'. 'Tifway II' is morphologically distinct (taller and coarser) from 'TifEagle' and the primer pair M-CAT/E-ACC was used to detect 10 DNA fragments unique to 'TifEagle' in the 320 to 500 bp range but not present in 'Tifway II'. 'TifEagle', 'Tifdwarf' and 'FloraDwarf' are more similar in growth habit. The primer pair M-CAT/E-ACC was used to identify three DNA fragments in the 210 to 325 bp range and two DNA fragments in the 600 to 640 bp range found in 'Tifdwarf' but not in 'TifEagle'. The primer pair M-CAA/E-AGG was used to identify three DNA fragments in the 600 to 640 bp range found in 'FloraDwarf' but not in 'TifEagle'.

In 7-week-old unmowed plots, green root-shoot weight of 'TifEagle' (8.65 g) was similar to 'Tifdwarf' (7.24 g) but significantly higher than that of 'FloraDwarf' (5.01 g). Number of shoots per 1963 $mm^2$ for 'TifEagle' (129) was significantly higher than for 'Tifdwarf' (103) but similar to 'FloraDwarf' (115). Shoot length of 'TifEagle' (17.8 mm) was significantly less than 'Tifdwarf' (22.5 mm) but similar to 'FloraDwarf' (17.7 mm). Leaves of 'TifEagle' (10.2 mm) were significantly shorter than those of 'Tifdwarf' (13.4 mm) but significantly longer than those of 'FloraDwarf' (7.5 mm). Leaves of 'TifEagle' (1.14 mm) were significantly narrower than those of 'Tifdwarf' (1.28 mm) but similar in width to those of 'FloraDwarf' (1.23 mm). Length of the first and third fully extended internodes of 'TifEagle' (10.5 and 10.3 mm) from the end of a juvenile stolon were significantly shorter than those of 'Tifdwarf' (13.2 and 11.8 mm) but similar to those of 'FloraDwarf' (9.5 and 10.2 mm), respectively.

In approximately one-year-old plots mowed at 6 mm, 'TifEagle' produced significantly more shoots (180) per 1963 $mm^2$ than 'Tifdwarf' (137) but a similar amount compared to 'FloraDwarf' (189). Green shoot-root weight was similar for 'TifEagle' (14.15 g), 'Tifdwarf' (15.94 g) and 'FloraDwarf' (14.67 g).

In addition, TifEagle bermudagrass demonstrates the following major characteristics:

Culm length is presented in Table 22 as shoot length. Culms average 2.9±0.4 leaves per node. Culm diameter is not presented because the very small diameter (1 mm or less) of 'TifEagle' culms precludes meaningful measurements to show differences among these dwarf bermudagrasses. Similarly, the average number of roots per node is also not presented. Roots per node can be affected by soil moisture, contact with soil, soil texture, etc. This high environmental variability makes comparison data unreliable and not meaningful.

Leaf blade length and width are given in Table 22. In addition, leaves are fine-textured and have a linear-lanceolate shape with short trichomes on the margin. The adaxial and abaxial leaf surfaces are glabrous.

Leaf sheath is glabrous. Sheaths on juvenile or new growth on stolons have a R.H.S. 59A color (Royal Horticultural Society). This color is not expressed in mature plant growth.

Ligule is a conspicuous ring of white hairs averaging 0.11±0.01 (mean±standard error) millimeters (mm) in length. Either end of ligule average 2.8±0.2 longer hairs that average 4.6±0.3 mm long.

Internode length for the first, second and third fully extended internodes beginning from the growing point of a stolon are given in Table 22 of the application.

Rhizome weights from 10 cm plugs were 14.1 and 15.9 g (5% LSD=2.9), respectively, for 'TifEagle' and 'Tifdwarf'.

Spike, spikelet, glum, and lemma data are not available because TifEagle has never flowered at the Tifton site.

TABLE A1

Turf quality of Tifdwarf and TifEagle bermudagrass mowed at 6 mm (¼ inch) at Tifton, Georgia (This is a yearly summary for the tests at Tifton, Georgia).

| | Quality* | | | | | | |
|---|---|---|---|---|---|---|---|
| | 1991 test** | | | | 1992 test | | |
| | 1992*** | 1993 | 1994 | 1995 | 1993 | 1994 | 1995 |
| Tifdwarf | 7.6 | 7.8 | 8.2 | 8.3 | 8.4 | 8.0 | 8.3 |
| TifEagle | 7.9 | 8.6 | 8.8 | 9.0 | 8.4 | 8.1 | 7.9 |
| 5% LSD | 0.4 | 0.4 | 0.4 | 0.5 | 0.5 | 0.6 | 0.8 |

| | Quality* | | | |
|---|---|---|---|---|
| | 1994 test | | 1995 test | |
| | 1995 | 1996 | 1995 | 1996 |
| Tifdwarf | 8.4 | 6.3 | 7.5 | 6.7 |
| TifEagle | 8.9 | 8.3 | 8.3 | 8.3 |
| 5% LSD | 0.9 | 0.7 | 0.9 | 0.8 |

*Ratings: 1 = poor, 9 = best
**Year planted
***Mean of yearly ratings

TABLE 1

1992 ratings on turf increase blocks of bermurdagrass hybrids established in 1991. (turfb92)

| | Quality | | | | | |
|---|---|---|---|---|---|---|
| Entry | 6/23 | 8/4* | 9/1 | 9/25 | 11/23 | Average |
| MI53 | 8.0 | 8.0 | 7.0 | 7.3 | 7.0 | 7.4 |
| Tifdwarf | 6.8 | 8.0 | 8.3 | 8.0 | 7.7 | 7.6 |
| Tifgreen | 7.0 | 7.5 | 7.0 | 7.3 | 6.7 | 7.2 |
| TW61 | 7.3 | 6.5 | 7.0 | 7.3 | 6.7 | 7.0 |

TABLE 1-continued 1992 ratings on turf increase blocks of bermurdagrass hybrids established in 1991. (turfb92)

| | Quality | | | | | |
|---|---|---|---|---|---|---|
| Entry | 6/23 | 8/4* | 9/1 | 9/25 | 11/23 | Average |
| Tifeagle | 8.0 | 8.0 | 8.3 | 8.0 | 7.7 | 7.9 |
| T582 | 8.0 | 7.0 | 8.0 | 8.0 | 8.3 | 7.9 |
| Anova | .0001 | .0357 | .0002 | .1119 | .0297 | .0072 |
| CV | 4 | 5 | 4 | 5 | 8 | 2 |
| 5% LSD | 0.4 | 0.9 | 0.5 | 0.7 | 1.0 | 0.4 |

Quality

1 = poor

9 = best

Note: Four random ratings were made on 10 m × 10 m increase blocks established in 1991. Mowed at 6 mm.

TABLE 2

1992 rating on turf increase blocks of bermudagrass hybrids hybrids established in l991. (turfb92)

| | Color | | | | |
|---|---|---|---|---|---|
| Entry | 11/23 | 12/4* | 12/10 | 1/11 | Average |
| MI53 | 4.0 | 3.7 | 3.0 | 2.3 | 3.3 |
| Tifdwarf | 4.0 | 2.0 | 1.0 | 2.3 | 2.3 |
| Tifgreen | 3.0 | 3.0 | 2.0 | 2.0 | 2.5 |
| TW61 | 3.0 | 2.3 | 2.3 | 2.0 | 2.4 |
| TifEagle | 4.0 | 3.0 | 2.0 | 3.7 | 3.2 |
| T582 | 5.0 | 5.0 | 5.0 | 3.3 | 4.6 |
| Anova | .0001 | .0001 | .0001 | .0028 | .0001 |
| CV | . | 11 | 9 | 17 | 5 |
| 5% LSD | . | 0.7 | 0.4 | 0.8 | 0.3 |

Color

1 = brown

5 = dark green

Note: Four randon ratings were made on 10 m × 10 m increase blocks established in 1991. Mowed at 6 mm.

TABLE 3

1993 quality ratings taken on turf increase blocks of bermudagrass hybrid planted in 1991. ((t95–96)(turfb93))

| | Quality | | | | | | |
|---|---|---|---|---|---|---|---|
| Entry | 4/23 | 06/9 | 7/16 | 9/16 | 10/19 | 11/23 | Average |
| MI53 | 7.8 | 8.0 | 7.5 | 6.0 | 7.8 | 9.0 | 7.7 |
| Tifdwarf | 7.5 | 8.0 | 7.8 | 8.0 | 8.0 | 7.8 | 7.8 |
| Tifgreen | 7.0 | 8.0 | 7.3 | 7.0 | 7.8 | 7.8 | 7.4 |
| TW61 | 7.3 | 8.5 | 7.0 | 6.5 | 6.8 | 6.5 | 7.1 |
| TifEagle | 8.3 | 8.8 | 8.8 | 9.0 | 8.5 | 8.5 | 8.6 |
| T582 | 8.5 | 8.0 | 8.3 | 8.8 | 9.0 | 9.0 | 8.6 |
| Anova | .0164 | .0155 | .0012 | .0001 | .0001 | .0001 | .0001 |
| CV | 7 | 4 | 6 | 7 | 5 | 6 | 3 |
| 5% LSD | .91 | .49 | .72 | .80 | .65 | .71 | .37 |

Quality ratings:

1 = poor

9 = best

Quality ratings on 11/23, some low quality ratings due to mole cricket damage.

Four randon ratings were made on 10 m × 10 m increase blocks established in 1991. Plots were mowed at 6 mm.

TABLE 4

1993 greenup, color and mole cricket damage ratings taken on turf increase blocks of bermudagrass hybrids planted in 1991. ((t95–96)(turfb93))

| | Greenup | Color | | | Mole cricket damage | | |
|---|---|---|---|---|---|---|---|
| Entry | 3/30 | 4/23 | 12/17 | Average | 10/20 | 12/17 | Average |
| MI53 | 2.0 | 4.0 | 5.5 | 4.8 | 1.0 | 1.0 | 1.0 |
| Tifdwarf | 3.3 | 5.0 | 4.0 | 4.5 | 3.5 | 4.8 | 4.1 |
| Tifgreen | 3.5 | 3.5 | 3.0 | 3.3 | 2.8 | 2.8 | 2.8 |
| TW61 | 1.5 | 3.8 | 3.8 | 3.8 | 2.5 | 5.3 | 3.9 |
| TifEagle | 3.8 | 5.0 | 3.0 | 4.0 | 3.3 | 4.3 | 3.8 |
| T582 | 2.5 | 4.0 | 7.0 | 5.5 | 1.8 | 1.5 | |
| Anova | .0001 | .0001 | .0001 | .0001 | .0001 | .0001 | .0001 |
| CV | 16 | 10 | 8 | 6 | 21 | 18 | 12 |
| 5% LSD | .67 | .44 | .49 | .40 | .79 | .34 | .52 |

Greenup ratings: Color ratings:

1 = brown 1 = brown

5 = green 5 = green

Mole cricket damage ratings on 10/20:

1 = no mole cricket damage

5 = susceptible

Mole cricket damage ratings on 12/17

1 = no mole cricket damage

9 = susceptible

Four random ratings were taken on 10 m × 10 m increase blocks established in 1991. Plots were mowed at 6 mm.

TABLE 5

1994 ratings on turf increase blocks of bermudagrass planted in 1991.(Turff94)

| | Quality | | | | | Color | | |
|---|---|---|---|---|---|---|---|---|
| Entry | 5/13 | 7/8 | 8/19 | 11/27 | Average | 11/27 | 12/31* | Average |
| Tifdwarf | 8.5 | 7.5 | 8.3 | 8.5 | 8.2 | 8.0 | 3.0 | 5.5 |
| Tifgreen | 8.0 | 5.3 | 7.0 | 6.3 | 6.6 | 6.5 | 2.0 | 4.3 |
| TifEagle | 8.8 | 8.5 | 9.0 | 9.0 | 8.8 | 7.8 | 2.5 | 5.1 |
| Anova | .1780 | .0004 | .0002 | .0005 | .0001 | .0027 | .8022 | .0478 |
| CV | 6 | 8 | 4 | 6 | 3 | 5 | 40 | 11 |
| 5% LSD | .86 | .95 | .49 | .86 | .39 | .64 | 1.73 | .97 |

| | Dollar spot | | Thatch |
|---|---|---|---|
| Entry | No Fungicide 2/3 | Fungicide | mm 1/11/95 |
| Tifdwarf | 1.5 | 1.0 | 15.1 |
| Tifgreen | 1.3 | 1.0 | 10.4 |
| TifEagle | 2.3 | 1.3 | 20.1 |
| Anova | .1537 | .4219 | .0001 |
| CV | 38 | 27 | 5 |
| 5% LSD | 1.1 | .49 | 1.4 |

Quality ratings: Color ratings:

1 = poor 11/27 12/31

9 = best 1 = brown 1 = brown

9 = green 5 = green

Fungicide Treatment Dollar spot:

1 = none

5 = 100%

*Color rating on 12/31 was rated after first light frost.

Four random ratings were made on 10 m × 10 m increase blocks established in 1991.

Plots were mowed at 6 mm.

TABLE 6

1995 ratings on (Oct. 5) on increase blocks of bermuagrass hybrids established in 1991. (turff95)

| Entry | Quality | Mole Cricket Damage |
|---|---|---|
| Tifdwarf | 8.3 | 3.0 |
| Tifgreen | 8.3 | 3.0 |
| TifEagle | 9.0 | 1.5 |
| Anova: Rep | .0701 | .1170 |
| Entry | .0156 | .0156 |
| CV | 3 | 23 |
| 5% LSD | 0.5 | 1.0 |

Quality ratings
1 = poor
9 = best

Mole Cricket Damage rating
0 = none
5 = susceptible

Note:
Four random ratings were made on 10 m × 10 m increase blocks established in 1991.

TABLE 7

1993 ratings on 1992 greens test planted 5/18/92. (Greent93)

| Entry | Green up 3/30 | Quality 4/23 | 6/9 | 7/16 | 9/16 | 10/19 | 11/23 | 12/17 | Average |
|---|---|---|---|---|---|---|---|---|---|
| MI22 | 2.0 | 7.0 | 7.5 | 8.0 | 7.0 | 8.0 | 8.0 | 7.5 | 7.6 |
| MI40 | 1.5 | 7.0 | 7.5 | 7.0 | 7.5 | 7.0 | 7.5 | 7.5 | 7.3 |
| MI43 | 1.5 | 8.0 | 8.5 | 7.5 | 7.0 | 7.5 | 7.0 | 7.5 | 4.6 |
| MI5 | 2.5 | 7.0 | 7.5 | 7.5 | 7.0 | 8.0 | 8.0 | 8.0 | 4.6 |
| Tifdwarf | 4.0 | 8.5 | 8.0 | 9.0 | 9.0 | 9.0 | 7.0 | 8.5 | 8.4 |
| Tifgreen | 3.0 | 8.0 | 7.0 | 8.0 | 7.0 | 7.5 | 8.0 | 8.0 | 7.6 |
| TW-61 | 2.0 | 7.5 | 7.5 | 7.0 | 7.0 | 5.5 | 5.0 | 5.0 | 6.4 |
| TifEagle | 4.0 | 8.5 | 8.5 | 9.0 | 7.5 | 8.5 | 8.0 | 9.0 | 8.4 |
| T501 | 1.0 | 6.5 | 7.0 | 7.5 | 6.0 | 7.0 | 7.0 | 7.5 | 6.9 |
| T504 | 3.5 | 8.0 | 7.0 | 5.5 | 8.0 | 8.0 | 7.5 | 8.5 | 7.5 |
| T513 | 2.0 | 7.5 | 7.0 | 7.0 | 7.0 | 8.0 | 7.5 | 9.0 | 7.6 |
| T529 | 3.0 | 7.0 | 6.0 | 6.0 | 6.5 | 5.5 | 6.5 | 6.0 | 6.2 |
| T54 | 2.5 | 6.5 | 5.5 | 6.0 | 6.0 | 5.0 | 4.5 | 5.5 | 5.6 |
| T562 | 2.0 | 7.5 | 7.5 | 7.0 | 7.0 | 7.0 | 7.0 | 7.5 | 7.2 |
| T563 | 2.0 | 7.0 | 6.0 | 5.0 | 5.0 | 6.0 | 6.5 | 7.0 | 6.1 |
| T570 | 4.5 | 9.0 | 8.5 | 9.0 | 9.0 | 9.0 | 8.0 | 9.0 | 8.8 |
| T7 | 2.0 | 7.0 | 8.0 | 8.0 | 6.5 | 7.5 | 7.5 | 7.5 | 7.4 |
| 559 | 2.0 | 6.0 | 6.0 | 6.0 | 6.5 | 5.5 | 6.0 | 6.0 | 6.0 |
| 72-117 | 2.0 | 7.5 | 7.0 | 7.5 | 6.5 | 6.5 | 8.0 | 7.5 | 7.2 |
| 72-16 | 1.5 | 7.5 | 7.5 | 7.5 | 6.5 | 8.0 | 8.0 | 8.5 | 4.6 |
| Anova | .0005 | .0391 | .0013 | .0001 | .0001 | .0001 | .0001 | .0001 | .0001 |
| CV | 25 | 9 | 8 | 8 | 7 | 10 | 7 | 7 | 3 |
| 5% LSD | 1.2 | 1.4 | 1.2 | 1.1 | .9 | 1.4 | 1.1 | 1.0 | 0.5 |

| Entry | Color 11/23 | 12/17 | Average | Mole cricket damage 10/20 | 12/17 | Average |
|---|---|---|---|---|---|---|
| MI22 | 4.0 | 5.0 | 4.5 | 1.5 | 1.5 | 1.5 |
| MI40 | 4.0 | 5.0 | 4.5 | 1.0 | 1.0 | 1.0 |
| MI43 | 4.0 | 5.0 | 4.5 | 1.5 | 2.0 | 1.8 |
| MI5 | 4.0 | 5.0 | 4.5 | 1.0 | 1.5 | 1.3 |
| Tifdwarf | 3.0 | 3.0 | 3.0 | 3.0 | 3.5 | 3.3 |
| Tifgreen | 3.5 | 4.0 | 3.8 | 3.0 | 3.5 | 3.3 |
| TW61 | 4.0 | 3.0 | 3.5 | 3.0 | 4.5 | 3.8 |
| TifEagle | 3.5 | 2.5 | 3.0 | 2.5 | 2.5 | 2.5 |
| T501 | 4.0 | 5.5 | 4.8 | 1.5 | 1.5 | 1.5 |
| T504 | 4.0 | 2.5 | 3.3 | 2.5 | 3.5 | 3.0 |
| T513 | 4.0 | 6.0 | 5.0 | 2.5 | 2.5 | 2.5 |

TABLE 7-continued 1993 ratings on 1992 greens test planted 5/18/92. (Greent93)

| | | | | | | |
|---|---|---|---|---|---|---|
| T529 | 3.0 | 6.0 | 4.5 | 1.5 | 2.0 | 1.8 |
| T54 | 3.5 | 5.0 | 4.3 | 3.0 | 3.0 | 3.0 |
| T562 | 4.0 | 4.5 | 4.3 | 1.5 | 2.0 | 1.8 |
| T563 | 3.0 | 3.0 | 3.0 | 2.0 | 1.5 | 1.8 |
| T570 | 4.0 | 2.0 | 3.0 | 2.5 | 2.5 | 2.5 |
| T7 | 4.0 | 5.0 | 4.5 | 1.0 | 1.0 | 1.0 |
| 559 | 2.0 | 5.0 | 3.5 | 1.0 | 1.0 | 1.0 |
| 72-117 | 4.0 | 5.0 | 4.5 | 1.0 | 1.0 | 1.0 |
| 72-16 | 4.0 | 5.0 | 4.5 | 1.0 | 1.0 | 1.0 |
| Anova | .0069 | .0001 | .0002 | .0027 | .0001 | .0002 |
| CV | 12 | 15 | 10 | 31 | 27 | 27 |
| 5% LSD | .8 | 1.3 | 0.8 | 1.2 | 1.2 | 1.2 |

green up ratings
1 = brown
5 = green quality ratings
1 = poor
9 = best

Color ratings
1 = brown
5 = green mole cricket damage ratings
1 = no mole crickets
5 = susceptible Quality ratings on 6/9 was rated before nitrogen applied.
Quality ratings on 11–23, some low quality rates due to mole cricket damage.
Test consisted of 2.6 m × 2.9 m plots with two replications.
Test cut at 6 mm.

TABLE 8

1994 ratings on 1992 greens test planted in 5-8-92. (greent94)

| Entry | Quality 5/13 | 7/8 | 8/19 | 11/27 | Average |
|---|---|---|---|---|---|
| MI22 | 8.5 | 7.0 | 6.0 | 7.0 | 7.1 |
| MI40 | 8.0 | 7.0 | 6.0 | 7.0 | 7.0 |
| MI43 | 7.5 | 7.0 | 6.0 | 6.5 | 6.8 |
| MI5 | 8.0 | 7.0 | 6.0 | 5.5 | 6.6 |
| Tifdwarf | 9.0 | 8.0 | 8.5 | 6.5 | 8.0 |
| Tifgreen | 8.0 | 6.0 | 6.5 | 7.5 | 7.0 |
| TW61 | 7.0 | 7.0 | 7.0 | 8.0 | 7.3 |
| TifEagle | 9.0 | 8.5 | 9.0 | 6.0 | 8.1 |
| T501 | 8.0 | 7.0 | 5.5 | 7.0 | 6.9 |
| T504 | 8.5 | 6.5 | 7.0 | 7.0 | 7.3 |
| T513 | 8.0 | 6.0 | 6.5 | 8.0 | 7.1 |
| T529 | 5.0 | 4.5 | 5.0 | 7.5 | 5.5 |
| T54 | 5.0 | 5.0 | 6.5 | 7.0 | 5.9 |
| T562 | 7.0 | 7.0 | 6.0 | 7.0 | 6.8 |
| T563 | 6.0 | 4.5 | 5.5 | 7.0 | 5.8 |
| T570 | 9.0 | 8.0 | 7.5 | 4.5 | 7.3 |
| T7 | 8.0 | 7.0 | 6.0 | 7.0 | 7.0 |
| 559 | 5.0 | 3.5 | 5.5 | 8.0 | 5.5 |
| 72-117 | 8.0 | 7.0 | 6.0 | 7.5 | 7.1 |
| 72-16 | 7.5 | 7.0 | 6.0 | 4.5 | 6.3 |
| Anova | .0165 | .7894 | .2585 | .3299 | .0001 |
| CV | 6 | 9 | 8 | 9 | 4 |
| 5% LSD | 1.0 | 1.2 | 1.1 | 1.3 | 0.6 |

| Entry | Color 2/11* | 11/27 | 12/31** | Average | Thatch 1/11/95 | Dollar spot 6/3 |
|---|---|---|---|---|---|---|
| MI22 | 1.5 | 7.0 | 4.0 | 4.2 | 12.0 | 1.0 |
| MI40 | 1.0 | 6.5 | 4.0 | 3.8 | 13.3 | 1.5 |
| MI43 | 1.5 | 6.5 | 4.0 | 4.0 | 11.8 | 1.0 |
| MI5 | 1.5 | 7.0 | 4.0 | 4.2 | 12.8 | 1.0 |
| Tifdwarf | 3.0 | 6.5 | 1.0 | 3.5 | 13.8 | 2.0 |
| Tifgreen | 3.0 | 7.0 | 2.0 | 4.0 | 11.3 | 1.5 |
| TW61 | 2.0 | 9.0 | 3.0 | 4.7 | 9.8 | 1.0 |
| TifEagle | 2.5 | 6.5 | 1.0 | 3.3 | 20.5 | 1.5 |
| T501 | 2.0 | 6.5 | 4.0 | 4.2 | 11.8 | 1.0 |
| T504 | 2.5 | 6.5 | 1.5 | 3.5 | 11.3 | 1.5 |
| T513 | 3.0 | 6.5 | 4.0 | 4.5 | 7.5 | 1.0 |
| T529 | 2.0 | 8.0 | 4.0 | 4.7 | 8.8 | 1.0 |
| T54 | 2.0 | 6.5 | 4.0 | 4.2 | 11.5 | 1.0 |

TABLE 8-continued 1994 ratings on 1992 greens test planted in 5-8-92. (green94)

| | | | | | | |
|---|---|---|---|---|---|---|
| T562 | 1.0 | 6.5 | 4.0 | 3.8 | 12.8 | 1.0 |
| T563 | 2.5 | 7.0 | 3.0 | 4.2 | 8.8 | 1.0 |
| T570 | 2.5 | 4.5 | 1.0 | 2.7 | 14.5 | 1.0 |
| T7 | 1.5 | 6.5 | 4.0 | 4.0 | 11.5 | 1.0 |
| 559 | 1.5 | 7.5 | 3.5 | 4.2 | 11.3 | 1.0 |
| 72-117 | 1.0 | 7.0 | 4.0 | 4.0 | 11.0 | 1.0 |
| 72-16 | 2.0 | 5.5 | 4.0 | 3.8 | 13.3 | 1.0 |
| Anova | .3299 | .0705 | .0553 | .0076 | .0625 | .3299 |
| CV | 24 | 11 | 15 | 9 | 18 | 27 |
| 5% LSD | 0.9 | 1.5 | 1.0 | 0.8 | 4.5 | 0.7 |

Quality ratings: Color ratings:
1 = poor 11/27 12/31 & 2/11
9 = best 1 = brown 1 = brown
9 = green 5 = green
Dollar spot ratings
1 = none
5 = 100%
Thatch thickness is in mm.
*Color ratings on 2/11 were made for greenup.
**Color ratings on 12/31 were made after first light frost.
Test consisted of 2.6 m × 2.9 m plots with two replications.

TABLE 9

1995 ratings on 1992 greens test. (Green95)

| | Quality on: | | | | |
|---|---|---|---|---|---|
| Entry | 5/25* | 7/11** | 10/4 | 11/9 | Average |
| MI22 | 7.5 | 8.0 | 8.0 | 7.5 | 7.8 |
| Tift 94 | 7.5 | 7.0 | 8.0 | 7.0 | 7.4 |
| MI43 | 7.5 | 8.0 | 7.5 | 7.0 | 7.5 |
| MI5 | 7.5 | 8.0 | 7.5 | 6.5 | 7.4 |
| Tifdwarf | 8.0 | 8.5 | 8.5 | 8.0 | 8.3 |
| Tifgreen | 7.5 | 7.0 | 7.0 | 7.0 | 7.1 |
| TW61 | 7.5 | 7.0 | 7.5 | 6.5 | 7.1 |
| TifEagle | 7.5 | 8.0 | 8.5 | 7.5 | 7.9 |
| T501 | 6.5 | 7.0 | 5.0 | 7.0 | 6.4 |
| T504 | 8.0 | 7.5 | 8.0 | 7.5 | 7.8 |
| T513 | 6.0 | 7.0 | 7.5 | 7.0 | 6.9 |
| T529 | 5.0 | 3.5 | 4.5 | 5.5 | 4.6 |
| T54 | 5.0 | 5.0 | 5.0 | 5.0 | 5.0 |
| T562 | 8.0 | 7.5 | 6.5 | 6.5 | 7.1 |
| T563 | 5.5 | 3.5 | 4.5 | 5.0 | 4.6 |
| T570 | 8.0 | 9.0 | 9.0 | 9.0 | 8.8 |
| T7 | 7.5 | 7.0 | 7.5 | 7.5 | 7.4 |
| 559 | 5.0 | 5.0 | 5.0 | 5.0 | 5.0 |
| 72-117 | 8.0 | 7.0 | 7.0 | 6.5 | 7.1 |
| 72-16 | 8.0 | 7.0 | 6.5 | 7.5 | 7.3 |
| Anova | | | | | |
| Rep | 1.0 | .8154 | .8252 | 1.0 | .8296 |
| Entry | .0001 | .0001 | .0001 | .0001 | .0001 |
| CV | 7 | 10 | 10 | 8 | 5 |
| 5% LSD | 1.1 | 1.4 | 1.5 | 1.1 | 0.8 |

| | Color on: | | | Mole Cricket Damage |
|---|---|---|---|---|
| Entry | 7/11 | 11/27+ | Average | 10/4 |
| MI22 | 8.0 | 7.0 | 7.5 | 0.0 |
| Tift 94 | 7.5 | 6.5 | 7.0 | 0.0 |
| MI43 | 7.5 | 7.0 | 7.3 | 0.0 |
| MI5 | 8.0 | 7.0 | 7.5 | 0.0 |
| Tifdwarf | 8.5 | 2.5 | 5.5 | 2.0 |
| Tifgreen | 6.5 | 3.0 | 4.8 | 2.5 |
| TW61 | 7.5 | 6.5 | 7.0 | 3.5 |
| TifEagle | 8.0 | 3.0 | 5.5 | 2.5 |
| T501 | 7.0 | 7.0 | 7.0 | 1.0 |
| T504 | 6.5 | 3.0 | 4.8 | 2.0 |
| T513 | 6.0 | 6.5 | 6.3 | 1.0 |

TABLE 9-continued 1995 ratings on 1992 greens test. (Green95)

| | | | | |
|---|---|---|---|---|
| T529 | 4.5 | 6.0 | 5.3 | 2.0 |
| T54 | 6.5 | 4.5 | 5.5 | 1.5 |
| T562 | 7.5 | 7.0 | 7.3 | 0.0 |
| T563 | 5.0 | 3.5 | 4.3 | 1.5 |
| T570 | 8.0 | 2.5 | 5.3 | 1.5 |
| T7 | 7.0 | 7.0 | 7.0 | 0.5 |
| 559 | 6.5 | 3.0 | 4.8 | 0.0 |
| 72-117 | 7.0 | 7.0 | 7.0 | 1.0 |
| 72-16 | 7.0 | 7.0 | 7.0 | 0.0 |
| Anova | | | | |
| Rep | .1189 | .3793 | .1021 | .5454 |
| Entry | .0051 | .0001 | .0001 | .0027 |
| CV | 11 | 10 | 8 | 68 |
| 5% LSD | 1.6 | 1.1 | 1.1 | 1.6 |

Quality ratings: Color ratings:
1 = poor 1 = brown
9 = best 9 = dark green
Mole cricket damage ratings:
0 = none
5 = worst
Greens were cut at 8 mm three times per week.
*Heading lowered ratings of some plots.
**Plots were low in nitrogen.
+rated after cold weather and light frosts.
Note:
Test consisted of 2.6 m × 2.9 m plots with two replications planted 5-18-92.

TABLE 10

1996 ratings for greenup and color on Turf bermudagrasses in 1992 green test. (Green96)

| | Rated April 7 | |
|---|---|---|
| Entry | Greenup | Color |
| MI22 | 7.0 | 8.0 |
| MI40 | 7.0 | 8.0 |
| NI43 | 7.0 | 7.5 |
| MI5 | 5.5 | 7.5 |
| Tifdwarf | 5.0 | 5.0 |
| Tifgreen | 4.0 | 4.5 |
| TW61 | 3.0 | 7.0 |
| TifEagle | 5.5 | 6.0 |
| T501 | 3.5 | 7.0 |
| T504 | 6.0 | 6.5 |
| T513 | 7.0 | 3.0 |
| T529 | 2.5 | 6.0 |
| T54 | 2.5 | 5.5 |
| T562 | 7.0 | 8.0 |
| T563 | 2.0 | 3.0 |
| T570 | 7.0 | 7.0 |
| T7 | 7.0 | 8.0 |
| 559 | 2.5 | 5.5 |
| 72-117 | 6.5 | 7.5 |
| 72-16 | 5.5 | 7.5 |
| range | 2–8 | 3–8 |
| Anova: | | |
| entry | .0001 | .0001 |
| rep | .1339 | .1864 |
| CV | 16 | 11 |
| 5% LSD | 1.7 | 1.4 |

Greenup: Color
1 = poor 1 = brown
9 = best 9 = dark green
*513 is nice but light green.
Note:
Test consisted of 2.6 m × 2.9 m plots with two replications mowed at 5 mm.
Planted on 5-18-92.

TABLE 11

1995 ratings on 1994 Very Dwarf Greens Test planted 5-23-94. (turf95b)

| | Quality on: | | | | | Color on: | | |
|---|---|---|---|---|---|---|---|---|
| Entry | 5/25* | 7/11** | 10/4 | 11/9 | Ave-rage | 7/11 | 11/27+ | Ave-rage |
| 1 | 8.0 | 5.5 | 6.0 | 6.0 | 6.4 | 7.5 | 6.5 | 7.0 |
| 2 | 7.0 | 6.0 | 6.0 | 6.0 | 6.3 | 7.0 | 4.0 | 5.5 |
| 3 | 6.0 | 5.5 | 5.5 | 6.0 | 5.8 | 6.0 | 7.0 | 6.5 |
| 4 | 6.5 | 6.0 | 7.0 | 8.0 | 6.9 | 7.0 | 8.0 | 7.5 |
| 5 | 7.0 | 5.5 | 6.0 | 6.5 | 6.3 | 6.0 | 7.0 | 6.5 |
| 6 | 7.0 | 5.5 | 5.0 | 5.0 | 5.6 | 6.0 | 6.5 | 6.3 |
| 7 | 7.0 | 7.5 | 7.0 | 7.5 | 7.3 | 7.5 | 8.0 | 7.8 |
| 8 | 6.5 | 5.5 | 7.0 | 7.0 | 6.5 | 7.5 | 5.5 | 6.5 |
| 9 | 7.0 | 6.5 | 5.5 | 5.0 | 6.0 | 6.0 | 5.0 | 5.5 |
| 10 | 7.0 | 7.5 | 7.5 | 6.5 | 7.1 | 7.0 | 6.5 | 6.8 |
| 11 | 7.5 | 6.5 | 6.0 | 5.0 | 6.3 | 7.0 | 6.5 | 6.8 |
| 12 | 6.5 | 6.5 | 7.0 | 7.5 | 6.9 | 7.0 | 4.0 | 5.5 |
| 13 | 6.5 | 7.5 | 5.5 | 7.5 | 6.8 | 6.0 | 7.0 | 6.5 |
| 14 | 7.5 | 7.0 | 5.0 | 5.5 | 6.3 | 6.5 | 7.0 | 6.8 |
| 15 | 4.5 | 5.0 | 5.0 | 7.5 | 5.5 | 6.0 | 6.0 | 6.0 |
| 16 | 7.5 | 7.0 | 6.5 | 7.0 | 7.0 | 6.0 | 6.5 | 6.3 |
| 17 | 6.5 | 6.0 | 6.0 | 6.5 | 6.3 | 6.5 | 6.5 | 6.5 |
| 18 | 8.5 | 9.0 | 8.0 | 8.5 | 8.5 | 9.0 | 7.0 | 8.0 |
| 19 | 7.0 | 6.0 | 7.0 | 7.0 | 6.8 | 7.0 | 7.5 | 7.3 |
| 20 | 5.5 | 5.5 | 5.0 | 6.0 | 5.5 | 7.0 | 6.0 | 6.5 |
| 21 | 7.0 | 8.0 | 8.5 | 8.0 | 7.9 | 8.0 | 8.0 | 8.0 |
| 22 | 7.0 | 8.0 | 4.5 | 5.5 | 6.3 | 8.0 | 5.5 | 6.8 |
| 23 | 5.5 | 5.5 | 6.5 | 7.5 | 6.3 | 7.0 | 6.5 | 6.8 |
| 24 | 7.0 | 7.0 | 6.0 | 6.5 | 6.6 | 6.0 | 6.5 | 6.3 |
| 25 | 8.5 | 9.0 | 7.0 | 7.0 | 7.9 | 8.0 | 4.5 | 6.3 |
| 26 | 6.0 | 6.0 | 5.5 | 7.0 | 6.1 | 8.0 | 6.5 | 7.3 |
| 27 | 6.5 | 6.0 | 8.0 | 8.0 | 7.1 | 6.5 | 3.5 | 5.0 |
| 28 | 7.0 | 6.0 | 6.5 | 7.0 | 6.6 | 6.5 | 7.0 | 6.8 |
| 29 | 7.0 | 7.0 | 6.0 | 6.5 | 6.6 | 6.5 | 7.0 | 6.8 |
| 30 | 7.0 | 6.5 | 7.0 | 8.0 | 7.1 | 7.5 | 8.0 | 7.8 |
| 31 | 5.5 | 6.5 | 6.5 | 8.0 | 6.6 | 8.5 | 6.5 | 7.5 |
| 32 | 7.0 | 6.0 | 7.5 | 7.5 | 7.0 | 6.5 | 5.0 | 5.8 |
| 33 | 7.0 | 6.5 | 7.0 | 6.0 | 6.6 | 7.5 | 5.5 | 6.5 |
| 34 | 8.0 | 6.0 | 6.0 | 5.5 | 6.4 | 7.0 | 5.5 | 6.3 |
| 35 | 7.0 | 5.0 | 5.5 | 5.5 | 5.8 | 6.0 | 6.0 | 6.0 |
| 36 | 6.5 | 7.0 | 6.0 | 6.0 | 6.4 | 7.5 | 5.0 | 6.3 |
| 37 | 7.5 | 5.0 | 5.0 | 6.5 | 6.0 | 6.0 | 6.0 | 6.0 |
| 38 | 7.0 | 5.5 | 6.0 | 5.0 | 5.9 | 6.5 | 4.0 | 5.3 |
| 39 | 6.0 | 6.0 | 6.5 | 7.5 | 6.5 | 6.5 | 7.5 | 7.0 |
| 40 | 6.0 | 6.0 | 6.5 | 6.5 | 6.3 | 7.5 | 7.5 | 7.5 |
| 41 | 6.5 | 7.0 | 6.5 | 7.0 | 6.8 | 7.0 | 7.0 | 7.0 |
| 42 | 6.5 | 8.0 | 6.0 | 7.0 | 6.9 | 6.5 | 7.5 | 7.0 |
| 43 | 7.5 | 8.0 | 4.5 | 5.5 | 6.4 | 7.0 | 7.0 | 7.0 |
| 44 | 7.0 | 6.0 | 7.0 | 8.0 | 7.0 | 8.0 | 7.5 | 7.8 |
| 45 | 7.0 | 5.0 | 6.0 | 6.0 | 6.0 | 7.0 | 6.0 | 6.5 |
| Tifdwarf | 8.5 | 9.0 | 8.5 | 7.5 | 8.4 | 9.0 | 3.0 | 6.0 |
| Tifgreen | 7.0 | 7.5 | 8.0 | 7.5 | 7.5 | 6.0 | 3.5 | 4.8 |
| TifEagle | 9.0 | 9.0 | 9.0 | 8.5 | 8.9 | 9.0 | 3.0 | 6.0 |
| Anova: | | | | | | | | |
| Rep | .0950 | .7612 | .4660 | .4291 | .6544 | .8299 | .0898 | .1470 |
| Entry | .0001 | .0001 | .0001 | .0001 | .0001 | .0001 | .0001 | .0001 |
| CV | 8 | 10 | 13 | 9 | 6 | 7 | 12 | 6 |
| 5% LSD | 1.1 | 1.3 | 1.7 | 1.3 | 0.9 | 0.9 | 1.4 | 0.8 |

Quality ratings: Color ratings:
1 = poor 1 = brown
9 = best 9 = dark green
Plots were cut at 6 mm three times per week.
*Heading lowered ratings of some plots.
**Plots were low on nitrogen.
+Rated after cold weather and light frosts.
Note:
Test consisted of 2.4 m × 2.7 m plots and two replications.

TABLE 12

1996 ratings on 1994 Very Dwarf Greens Test planted on 5-23-94. (Turf96b)

| | Greenup | Color | | | % Seed Heading | Mole Cricket damage |
|---|---|---|---|---|---|---|
| Entry | 4/7 | 4/7 | 6/13 | Ave. | 5/15 | 10/15 |
| 1 | 6.5 | 7.5 | 7.5 | 7.5 | 3.5 | 1.0 |
| 2 | 7.5 | 6.0 | 7.0 | 6.5 | 1.5 | 1.0 |
| 3 | 5.5 | 8.0 | 6.5 | 7.3 | 4.5 | 1.0 |
| 4 | 7.0 | 8.0 | 7.0 | 7.5 | 4.5 | 1.5 |
| 5 | 5.0 | 8.0 | 7.0 | 7.5 | 3.5 | 1.0 |
| 6 | 6.5 | 8.0 | 6.5 | 7.3 | 5.0 | 1.0 |
| 7 | 6.5 | 6.5 | 7.5 | 7.0 | 3.0 | 1.0 |
| 8 | 6.0 | 8.5 | 7.5 | 8.0 | 5.0 | 1.0 |
| 9 | 3.5 | 7.0 | 6.0 | 6.5 | 1.0 | 1.0 |
| 10 | 7.0 | 7.0 | 6.0 | 6.5 | 4.5 | 1.0 |
| 11 | 5.0 | 6.0 | 7.0 | 6.5 | 1.0 | 4.5 |
| 12 | 5.5 | 5.0 | 7.0 | 6.0 | 5.0 | 1.0 |
| 13 | 6.0 | 7.5 | 7.0 | 7.3 | 7.0 | 2.0 |
| 14 | 4.5 | 8.0 | 7.0 | 7.5 | 3.5 | 1.0 |
| 15 | 4.5 | 5.0 | 6.0 | 5.5 | 2.0 | 1.0 |
| 16 | 6.0 | 8.0 | 6.0 | 7.0 | 6.0 | 1.0 |
| 17 | 5.5 | 7.5 | 7.0 | 7.3 | 6.0 | 1.0 |
| 18 | 6.5 | 7.0 | 9.0 | 8.0 | 1.5 | 1.0 |
| 19 | 6.0 | 8.0 | 7.0 | 7.5 | 3.5 | 1.5 |
| 20 | 6.0 | 8.0 | 7.0 | 7.5 | 4.0 | 1.0 |
| 21 | 7.0 | 7.5 | 8.0 | 7.8 | 4.0 | 1.5 |
| 22 | 4.5 | 5.5 | 8.0 | 6.8 | 3.0 | 2.0 |
| 23 | 3.5 | 4.0 | 6.0 | 5.0 | 1.0 | 1.0 |
| 24 | 6.0 | 7.0 | 7.0 | 7.0 | 3.5 | 1.0 |
| 25 | 7.0 | 6.5 | 8.0 | 7.3 | 1.0 | 1.0 |
| 26 | 4.5 | 4.5 | 8.0 | 6.3 | 2.5 | 1.0 |
| 27 | 6.5 | 6.0 | 7.0 | 6.5 | 2.5 | 1.0 |
| 28 | 6.5 | 8.0 | 6.5 | 7.3 | 6.5 | 2.5 |
| 29 | 6.5 | 8.0 | 6.5 | 7.3 | 4.0 | 1.0 |
| 30 | 7.0 | 5.5 | 7.0 | 6.3 | 3.0 | 1.0 |
| 31 | 6.5 | 5.5 | 7.5 | 6.5 | 2.5 | 2.5 |
| 32 | 6.5 | 6.5 | 6.5 | 6.5 | 3.5 | 1.0 |
| 33 | 5.0 | 7.0 | 7.5 | 7.3 | 3.0 | 1.0 |
| 34 | 5.0 | 8.0 | 8.0 | 8.0 | 1.5 | 2.5 |
| 35 | 5.5 | 8.0 | 7.0 | 7.5 | 6.5 | 1.0 |
| 36 | 4.5 | 5.5 | 7.0 | 6.3 | 1.0 | 1.0 |
| 37 | 6.0 | 8.0 | 6.5 | 7.3 | 6.0 | 1.0 |
| 38 | 5.0 | 7.0 | 7.5 | 7.3 | 1.0 | 1.0 |
| 39 | 6.0 | 7.0 | 6.5 | 6.8 | 2.0 | 2.0 |
| 40 | 6.0 | 6.5 | 7.5 | 7.0 | 5.0 | 3.0 |
| 41 | 6.5 | 8.0 | 8.0 | 8.0 | 4.5 | 1.0 |
| 42 | 6.5 | 8.0 | 6.5 | 7.3 | 7.5 | 1.0 |
| 43 | 7.0 | 8.0 | 7.5 | 7.8 | 7.0 | 1.0 |
| 44 | 6.5 | 8.0 | 7.0 | 7.5 | 4.5 | 1.0 |
| 45 | 7.0 | 8.5 | 7.5 | 8.0 | 3.5 | 1.0 |
| Tifdwarf | 6.5 | 6.0 | 8.5 | 7.3 | 1.0 | 9.0 |
| Tifgreen | 8.0 | 7.5 | 7.0 | 7.3 | 2.0 | 7.5 |
| TifEagle | 7.5 | 7.0 | 8.0 | 7.5 | 1.0 | 4.0 |
| Anova | | | | | | |
| Entry | .0001 | .0001 | .0001 | .0001 | .0001 | .0001 |
| Rep | .4519 | .8165 | .0487 | .3884 | .0227 | .0063 |
| CV | 13 | 12 | 7 | 7 | 21 | 47 |
| 5% LSD | 1.6 | 1.8 | 1.0 | 0.9 | 1.5 | 1.6 |

| Mole cricket damage | |
|---|---|
| Entry | 8/02 |
| Tifdwarf | 8.5 |
| Tifgreen | 6.5 |
| TW72 | 3.0 |
| Anova | .1226 |
| CV | 25 |
| 5% LSD | 6.3 |

Greenup Color % Seed Heading
1 = poor 1 = brown 1 = no heads
9 = best 9 = dark green 9 = complete heads exserted
Mole cricket damage Dollar Spot
1 = none 1 = none
9 = susceptible 5 = susceptible
4/07/96 - #11 very susceptible to mole cricket (rated 3)

TABLE 12-continued 1996 ratings on 1994 Very Dwarf Greens Test planted on 5-23-94. (Turf96b)

6/13/96 - low on nitrogen

6/13/96 - on this date many low ratings due to heading

8/02/96 - low on nitrogen

8/23/96 - mower raised after this rating

Note:

Test consisted of 2.4 m × 2.7 m plots and two replications mowed at 6 mm.

TABLE 13

1996 ratings on 1994 Very Dwarf Greens Test planted on 5-23-94. (Turf96b)

| | Quality | | | | | |
|---|---|---|---|---|---|---|
| Entry | 6/13 | 8/2 | 8/23 | 9/12 | 10/15 | Average |
| 1 | 6.0 | 4.5 | 4.5 | 4.5 | 6.0 | 5.1 |
| 2 | 7.0 | 5.5 | 5.0 | 6.5 | 5.5 | 5.9 |
| 3 | 6.0 | 5.0 | 5.5 | 6.0 | 5.5 | 5.6 |
| 4 | 6.0 | 6.0 | 6.0 | 6.5 | 7.5 | 6.4 |
| 5 | 6.0 | 5.0 | 5.0 | 5.0 | 5.0 | 5.2 |
| 6 | 7.0 | 4.0 | 3.5 | 4.5 | 4.5 | 4.7 |
| 7 | 6.0 | 6.0 | 6.5 | 7.5 | 7.0 | 6.6 |
| 8 | 5.5 | 5.0 | 6.0 | 5.5 | 6.0 | 5.6 |
| 9 | 6.0 | 5.0 | 4.0 | 7.5 | 4.5 | 5.4 |
| 10 | 7.0 | 5.5 | 4.5 | 6.0 | 6.5 | 5.9 |
| 11 | 6.5 | 5.5 | 6.0 | 5.0 | 5.5 | 5.7 |
| 12 | 5.5 | 5.5 | 4.5 | 5.0 | 6.0 | 5.3 |
| 13 | 6.0 | 5.5 | 5.5 | 6.0 | 6.0 | 5.8 |
| 14 | 5.0 | 5.0 | 6.0 | 6.0 | 6.5 | 5.7 |
| 15 | 5.0 | 4.0 | 3.0 | 3.5 | 5.5 | 4.2 |
| 16 | 7.0 | 6.0 | 6.5 | 6.5 | 8.0 | 6.8 |
| 17 | 6.0 | 5.5 | 6.5 | 6.0 | 6.5 | 6.1 |
| 18 | 6.5 | 7.0 | 7.0 | 7.5 | 9.0 | 7.4 |
| 19 | 6.5 | 6.5 | 6.0 | 6.0 | 7.0 | 6.4 |
| 20 | 5.5 | 5.5 | 5.0 | 4.5 | 5.5 | 5.2 |
| 21 | 8.0 | 6.0 | 5.0 | 6.5 | 8.5 | 6.8 |
| 22 | 7.0 | 6.5 | 6.5 | 7.0 | 6.5 | 6.7 |
| 23 | 4.5 | 3.5 | 5.0 | 4.5 | 5.0 | 4.5 |
| 24 | 6.5 | 5.5 | 6.0 | 6.5 | 6.5 | 6.2 |
| 25 | 8.0 | 6.0 | 5.0 | 7.5 | 6.0 | 6.5 |
| 26 | 5.5 | 5.5 | 5.5 | 5.0 | 6.0 | 5.5 |
| 27 | 5.5 | 5.5 | 6.0 | 5.5 | 5.0 | 5.5 |
| 28 | 7.0 | 5.5 | 6.5 | 6.0 | 6.5 | 6.3 |
| 29 | 8.0 | 6.5 | 6.5 | 7.0 | 6.5 | 6.9 |
| 30 | 6.0 | 5.5 | 4.5 | 6.0 | 7.0 | 5.8 |
| 31 | 5.5 | 6.0 | 4.5 | 6.5 | 6.5 | 5.8 |
| 32 | 6.0 | 5.0 | 5.5 | 5.5 | 6.5 | 5.7 |
| 33 | 5.5 | 6.0 | 6.0 | 7.5 | 8.0 | 6.6 |
| 34 | 8.0 | 6.0 | 5.0 | 6.0 | 5.5 | 6.1 |
| 35 | 5.5 | 5.0 | 5.0 | 5.5 | 4.5 | 5.1 |
| 36 | 7.0 | 5.5 | 5.0 | 6.0 | 6.5 | 6.0 |
| 37 | 6.5 | 4.0 | 5.0 | 4.0 | 4.0 | 4.7 |
| 38 | 5.0 | 5.0 | 5.0 | 4.5 | 4.0 | 4.7 |
| 39 | 7.0 | 6.0 | 5.0 | 6.0 | 6.0 | 6.0 |
| 40 | 5.5 | 5.0 | 5.0 | 5.5 | 5.5 | 5.3 |
| 41 | 7.0 | 6.0 | 4.5 | 6.5 | 8.5 | 6.5 |
| 42 | 6.0 | 6.5 | 5.0 | 7.0 | 8.0 | 6.5 |
| 43 | 6.5 | 6.5 | 5.5 | 6.5 | 5.5 | 6.1 |
| 44 | 6.0 | 5.5 | 5.0 | 6.5 | 6.5 | 5.9 |
| 45 | 6.5 | 4.5 | 5.0 | 5.5 | 6.5 | 5.6 |
| Tifdwarf | 7.0 | 7.0 | 6.0 | 5.0 | 6.5 | 6.3 |
| Tifgreen | 7.0 | 6.5 | 5.5 | 5.0 | 7.0 | 6.2 |
| TifEagle | 8.5 | 8.5 | 8.5 | 7.5 | 8.5 | 8.3 |
| Anova | | | | | | |
| Entry | .0001 | .0001 | .0191 | .0001 | .0001 | .0001 |
| Rep | 1.0 | .0001 | .0002 | .0002 | .6423 | .0001 |

TABLE 13-continued 1996 ratings on 1994 Very Dwarf Greens Test planted on 5-23-94. (Turf96b)

| | Quality | | | | | |
|---|---|---|---|---|---|---|
| Entry | 6/13 | 8/2 | 8/23 | 9/12 | 10/15 | Average |
| CV | 8 | 9 | 18 | 12 | 14 | 6 |
| 5% LSD | 1.1 | 1.1 | 2.0 | 1.4 | 1.8 | 0.7 |

Quality 1 = poor, 9 = good
6/13/96 - low on nitrogen
6/13/96 - on this date many low rates due to heading
8/2/96 - low on nitrogen
8/23/96 - mower raised after this rating
Note:
Test consisted of 2.4 m × 2.7 m plots and two replications mowed at 6 mm.

TABLE 14

1995 ratings for mole cricket damage, quality and color on 1995 Greens Test planted 4-7-95. (Tifdwf95)

| | Quality | | | Color | Mole Cricket Damage |
|---|---|---|---|---|---|
| Entry | 10/5 | 11/9 | Ave. | 11/27 | 10/5 |
| Tift 94 | 7.0 | 7.5 | 7.3 | 8.0 | 1.0 |
| Tifdwarf | 7.5 | 7.5 | 7.5 | 2.5 | 2.5 |
| Tifgreen | 5.5 | 6.0 | 5.8 | 3.5 | 2.5 |
| TifEagle | 8.5 | 8.0 | 8.3 | 3.5 | 3.0 |
| T513 | 5.5 | 7.0 | 6.3 | 6.5 | 1.0 |
| T557 | 5.0 | 6.0 | 5.5 | 3.5 | 2.0 |
| T568 | 6.0 | 6.5 | 6.3 | 3.5 | 3.5 |
| T569 | 6.5 | 5.5 | 6.0 | 2.5 | 3.0 |
| T589 | 5.5 | 5.5 | 5.5 | 3.5 | 2.5 |
| 261 | 6.0 | 6.0 | 6.0 | 6.0 | 0.0 |
| 262 | 7.0 | 6.5 | 6.8 | 6.5 | 1.5 |
| 273 | 7.0 | 7.0 | 7.0 | 6.5 | 0.5 |
| 275 | 7.5 | 7.5 | 7.5 | 7.0 | 1.0 |
| 290 | 5.0 | 5.0 | 5.0 | 5.5 | 1.0 |
| 291 | 7.5 | 7.5 | 7.5 | 4.5 | 0.5 |
| 306 | 6.5 | 7.0 | 6.8 | 6.0 | 1.0 |
| 307 | 5.5 | 6.5 | 6.0 | 5.0 | 1.0 |
| 313 | 7.0 | 7.0 | 7.0 | 6.5 | 1.5 |
| 326 | 6.0 | 6.0 | 6.0 | 7.0 | 1.5 |
| 343 | 6.5 | 6.0 | 6.3 | 6.0 | 1.5 |
| 344 | 7.5 | 6.0 | 6.8 | 6.0 | 0.0 |
| 345 | 6.5 | 6.5 | 6.5 | 6.0 | 0.5 |
| 347 | 7.5 | 6.5 | 7.0 | 6.5 | 1.0 |
| 350 | 7.0 | 7.5 | 7.3 | 4.0 | 1.5 |
| 354 | 7.0 | 7.0 | 7.0 | 6.5 | 1.0 |
| 355 | 8.5 | 7.5 | 8.0 | 3.0 | 2.0 |
| 368 | 6.5 | 6.5 | 6.5 | 6.0 | 0.0 |
| 378 | 7.5 | 6.0 | 6.8 | 4.0 | 0.0 |
| 379 | 8.0 | 8.0 | 8.0 | 3.0 | 0.0 |
| 384 | 5.0 | 5.5 | 5.3 | 5.5 | 0.0 |
| 389 | 6.0 | 7.0 | 6.5 | 5.5 | 0.5 |
| 396 | 7.0 | 5.5 | 6.3 | 4.5 | 1.0 |
| 400 | 8.0 | 7.0 | 7.5 | 7.0 | 0.5 |
| 416 | 6.5 | 6.5 | 6.5 | 6.0 | 1.5 |
| 423 | 7.5 | 6.5 | 7.0 | 6.0 | 1.0 |
| 442 | 7.5 | 6.5 | 7.0 | 6.0 | 0.5 |
| 451 | 7.5 | 7.0 | 7.3 | 7.0 | 0.5 |
| 452 | 5.5 | 6.0 | 5.8 | 6.5 | 0.5 |
| 453 | 6.5 | 6.5 | 6.5 | 6.0 | 0.0 |
| 454 | 6.4 | 5.5 | 6.0 | 5.5 | 0.0 |
| 455 | 6.5 | 6.5 | 6.5 | 6.0 | 0.0 |
| 456 | 6.5 | 6.5 | 6.5 | 6.0 | 1.0 |
| 457 | 8.5 | 7.0 | 7.8 | 7.0 | 0.5 |
| 458 | 6.0 | 5.5 | 5.8 | 5.0 | 2.5 |
| 459 | 5.5 | 5.5 | 5.5 | 6.0 | 0.0 |
| 460 | 8.0 | 7.0 | 7.5 | 7.0 | 0.5 |
| 461 | 6.5 | 5.5 | 6.0 | 5.5 | 1.5 |
| 462 | 5.5 | 6.0 | 5.8 | 5.5 | 0.0 |

TABLE 14-continued 1995 ratings for mole cricket damage, quality and color on 1995 Greens Test planted 4-7-95. (Tifdwf95)

| | Quality | | | Color | Mole Cricket Damage |
|---|---|---|---|---|---|
| Entry | 10/5 | 11/9 | Ave. | 11/27 | 10/5 |
| 463 | 6.5 | 6.5 | 6.5 | 6.0 | 1.0 |
| 464 | 6.5 | 6.0 | 6.3 | 5.5 | 2.0 |
| 466 | 6.5 | 6.0 | 6.3 | 6.0 | 0.5 |
| 468 | 6.0 | 6.0 | 6.0 | 6.0 | 0.5 |
| 469 | 6.0 | 6.0 | 6.0 | 6.0 | 0.0 |
| 475 | 6.5 | 6.5 | 6.5 | 6.0 | 1.0 |
| 477 | 8.0 | 7.0 | 7.5 | 7.0 | 0.5 |
| 478 | 7.0 | 7.0 | 7.0 | 7.0 | 0.0 |
| 480 | 7.0 | 7.0 | 7.0 | 7.0 | 1.0 |
| 482 | 7.0 | 6.5 | 6.8 | 6.5 | 1.0 |
| 483 | 5.0 | 5.5 | 5.3 | 5.5 | 1.5 |
| 484 | 6.5 | 6.5 | 6.5 | 6.5 | 0.5 |
| 485 | 6.0 | 6.0 | 6.0 | 6.0 | 0.5 |
| 487 | 6.0 | 6.0 | 6.0 | 6.0 | 1.5 |
| 488 | 6.5 | 6.0 | 6.3 | 6.5 | 1.5 |
| 489 | 6.5 | 6.5 | 6.5 | 6.5 | 0.5 |
| Anova: | | | | | |
| Rep | .8920 | 1.0 | .9253 | .0113 | .0006 |
| Entry | .0001 | .0001 | .0001 | .0001 | .0001 |
| CV | 10 | 9 | 7 | 12 | 76 |
| 5% LSD | 1.3 | 1.2 | 0.9 | 1.3 | 1.5 |

Quality ratings: Color ratings:
1 = poor 1 = brown
9 = best 9 = dark green
Mole cricket damage 10/5
0 = none
5 = susceptable
Note:
Test consisted of 2.4 m × 2.4 m plots and two replications mowed at 6 mm.

TABLE 15

1996 quality ratings on 1994 dwarf bermundagrass selections in 1995 Greens Test planted on 4/7/95. (tifdwf96)

| | Quality | | | | | |
|---|---|---|---|---|---|---|
| Entry | 6/13 | 8/2 | 8/23 | 9/12 | 10/15 | Average |
| T513 | 6.0 | 6.0 | 4.5 | 6.0 | 5.5 | 5.6 |
| T557 | 6.0 | 5.0 | 5.0 | 4.0 | 5.5 | 5.1 |
| T568 | 5.5 | 6.0 | 5.5 | 5.5 | 6.0 | 5.7 |
| T569 | 5.5 | 5.0 | 5.0 | 5.0 | 5.5 | 5.2 |
| T589 | 5.5 | 6.0 | 6.0 | 5.0 | 6.5 | 5.8 |
| 261 | 6.0 | 4.0 | 4.5 | 5.5 | 6.0 | 5.2 |
| 262 | 5.5 | 5.5 | 6.0 | 5.5 | 6.0 | 5.7 |
| 273 | 5.5 | 6.0 | 6.0 | 6.0 | 6.5 | 6.0 |
| 275 | 6.0 | 5.0 | 6.0 | 7.0 | 6.0 | 6.0 |
| 290 | 4.5 | 3.5 | 5.5 | 3.0 | 4.0 | 4.1 |
| 291 | 5.0 | 5.5 | 5.5 | 6.0 | 6.5 | 5.7 |
| 306 | 7.5 | 7.5 | 7.5 | 7.0 | 7.0 | 7.3 |
| 307 | 5.0 | 5.5 | 6.0 | 4.0 | 4.5 | 5.0 |
| 313 | 6.0 | 4.5 | 5.5 | 6.0 | 7.0 | 5.8 |
| 326 | 5.5 | 5.0 | 5.5 | 4.5 | 5.0 | 5.1 |
| 343 | 5.0 | 5.5 | 5.5 | 6.5 | 5.5 | 5.6 |
| 344 | 6.0 | 5.0 | 6.5 | 6.5 | 5.5 | 5.9 |
| 345 | 5.0 | 4.0 | 6.0 | 4.0 | 4.5 | 4.7 |
| 347 | 5.0 | 5.5 | 6.5 | 6.0 | 7.5 | 6.1 |
| 350 | 5.0 | 5.5 | 7.0 | 6.0 | 7.0 | 6.1 |
| 354 | 5.0 | 5.0 | 6.0 | 6.0 | 6.5 | 5.7 |
| 355 | 8.0 | 9.0 | 7.0 | 6.5 | 8.5 | 7.8 |
| 368 | 6.5 | 6.0 | 4.5 | 7.5 | 5.5 | 6.0 |
| 378 | 6.5 | 6.0 | 6.0 | 6.0 | 7.0 | 6.3 |
| 379 | 5.5 | 5.5 | 6.5 | 5.5 | 4.5 | 5.5 |
| 384 | 5.0 | 3.5 | 4.5 | 5.5 | 4.5 | 4.6 |
| 389 | 5.0 | 5.0 | 6.0 | 7.5 | 7.5 | 6.2 |

TABLE 15-continued 1996 quality ratings on 1994 dwarf bermundagrass selections in 1995 Greens Test planted on 4/7/95. (tifdwf96)

| | Quality | | | | | |
|---|---|---|---|---|---|---|
| Entry | 6/13 | 8/2 | 8/23 | 9/12 | 10/15 | Average |
| 396 | 5.5 | 5.5 | 6.0 | 6.5 | 5.0 | 5.7 |
| 400 | 6.0 | 5.5 | 5.5 | 7.0 | 7.0 | 6.2 |
| 416 | 5.0 | 6.0 | 5.5 | 5.5 | 5.5 | 5.5 |
| 423 | 6.5 | 4.5 | 4.5 | 4.5 | 5.5 | 5.1 |
| 442 | 6.0 | 5.5 | 6.5 | 7.0 | 6.0 | 6.2 |
| 451 | 6.0 | 6.0 | 6.5 | 6.5 | 7.5 | 6.5 |
| 452 | 5.0 | 4.5 | 6.5 | 4.5 | 4.5 | 5.0 |
| 453 | 7.0 | 6.5 | 5.5 | 7.0 | 6.0 | 6.4 |
| 454 | 5.0 | 4.5 | 6.0 | 6.0 | 5.5 | 5.4 |
| 455 | 6.5 | 4.0 | 5.0 | 5.5 | 5.0 | 5.2 |
| 456 | 5.0 | 4.5 | 6.5 | 6.0 | 6.0 | 5.6 |
| 457 | 6.0 | 5.0 | 6.5 | 6.5 | 7.0 | 6.2 |
| 458 | 4.5 | 4.5 | 6.5 | 4.5 | 5.5 | 5.1 |
| 459 | 6.0 | 3.5 | 5.0 | 4.5 | 4.5 | 4.7 |
| 460 | 6.0 | 5.5 | 6.5 | 6.5 | 8.5 | 6.6 |
| 461 | 5.0 | 4.0 | 6.0 | 5.0 | 4.5 | 4.9 |
| 462 | 6.5 | 6.0 | 4.5 | 5.5 | 5.5 | 5.6 |
| 463 | 7.5 | 5.5 | 4.5 | 6.5 | 6.5 | 6.1 |
| 464 | 5.0 | 5.0 | 5.5 | 5.5 | 5.0 | 5.2 |
| 466 | 5.5 | 5.0 | 5.0 | 6.0 | 5.5 | 5.4 |
| 468 | 5.5 | 5.0 | 5.0 | 5.5 | 5.0 | 5.2 |
| 469 | 5.5 | 6.0 | 5.0 | 6.0 | 6.0 | 5.7 |
| 475 | 5.0 | 5.5 | 6.0 | 5.5 | 5.5 | 5.5 |
| 477 | 7.0 | 7.0 | 8.0 | 6.5 | 7.5 | 7.2 |
| 478 | 6.0 | 5.5 | 6.0 | 5.5 | 6.0 | 5.8 |
| 480 | 6.0 | 6.0 | 7.5 | 7.0 | 7.5 | 6.8 |
| 482 | 6.5 | 6.0 | 7.0 | 6.5 | 6.5 | 6.5 |
| 483 | 5.5 | 5.5 | 5.0 | 6.0 | 5.0 | 5.4 |
| 484 | 5.5 | 5.0 | 6.5 | 7.0 | 8.0 | 6.4 |
| 485 | 6.5 | 5.5 | 4.5 | 5.0 | 4.0 | 5.1 |
| 487 | 5.5 | 6.0 | 6.5 | 7.0 | 7.0 | 6.4 |
| 488 | 5.0 | 5.0 | 5.5 | 5.5 | 5.5 | 5.3 |
| 489 | 5.5 | 6.0 | 6.0 | 5.0 | 6.5 | 5.8 |
| MI40 | 8.0 | 7.5 | 5.5 | 6.5 | 7.5 | 7.0 |
| Tifdwarf | 6.5 | 8.0 | 6.0 | 6.0 | 7.0 | 6.7 |
| Tifgreen | 6.0 | 6.0 | 5.5 | 5.0 | 5.5 | 5.6 |
| TifEagle | 9.0 | 9.0 | 8.0 | 7.0 | 8.5 | 8.3 |
| range | 4–9 | 3–9 | 4–8 | 3–8 | 3–9 | 3–9 |
| Anova | | | | | | |
| Entry | .0001 | .0001 | .0001 | .0009 | .0001 | .0001 |
| Rep | .1292 | 1.0 | .8976 | .0414 | .3353 | .3653 |
| CV | 9 | 14 | 12 | 15 | 15 | 7 |
| 5% LSD | 1.0 | 1.6 | 1.4 | 1.8 | 1.8 | 0.8 |

Quality
1 = poor
9 = good
6/13 - low on nitrogen
8/23 - Height on mower raised after rating
Note:
Test consisted of 2.4 m × 2.4 m plots and two replications mowed at 6 mm.

TABLE 16

1996 greenup, color, % seed heads and mole cricket damage ratings on dwarf bermudagrass selections in 1995 Greens Test planted 4-7-95. (tifdwf96)

| Entry | Green up 4/7 | Color 4/7 | % Seed Heading 5/15 | Mole Cricket Damage 10/15 |
|---|---|---|---|---|
| T513 | 6.0 | 4.0 | 6.5 | 3.5 |
| T557 | 4.0 | 6.5 | 3.0 | 8.0 |
| T568 | 4.0 | 8.0 | 1.5 | 7.5 |
| T569 | 3.5 | 6.0 | 2.0 | 9.0 |
| T589 | 5.0 | 7.5 | 1.5 | 8.0 |
| 261 | 6.0 | 7.5 | 4.0 | 1.5 |

TABLE 16-continued 1996 greenup, color, % seed heads and mole cricket damage ratings on dwarf bermudagrass selections in 1995 Greens Test planted 4-7-95. (tifdwf96)

| | | | | |
|---|---|---|---|---|
| 262 | 5.5 | 8.0 | 6.0 | 3.0 |
| 273 | 5.5 | 8.0 | 6.0 | 1.5 |
| 275 | 5.0 | 8.0 | 4.5 | 2.0 |
| 290 | 5.0 | 8.0 | 5.5 | 1.0 |
| 291 | 5.0 | 4.0 | 2.0 | 3.0 |
| 306 | 5.5 | 7.5 | 4.5 | 2.5 |
| 307 | 2.5 | 3.0 | 1.0 | 3.5 |
| 313 | 5.5 | 8.0 | 1.5 | 2.5 |
| 326 | 6.0 | 8.0 | 2.5 | 2.5 |
| 343 | 6.0 | 8.0 | 6.5 | 1.0 |
| 344 | 5.5 | 4.0 | 4.0 | 2.0 |
| 345 | 5.5 | 8.0 | 4.0 | 2.0 |
| 347 | 6.0 | 7.0 | 4.0 | 1.5 |
| 350 | 3.5 | 4.0 | 3.5 | 2.5 |
| 354 | 6.0 | 8.0 | 5.5 | 2.0 |
| 355 | 6.5 | 7.0 | 1.0 | 6.0 |
| 368 | 5.5 | 8.0 | 4.5 | 1.5 |
| 378 | 5.5 | 8.5 | 3.0 | 1.0 |
| 379 | 6.0 | 4.5 | 2.0 | 3.5 |
| 384 | 5.0 | 7.5 | 4.5 | 1.0 |
| 389 | 2.5 | 5.5 | 1.5 | 1.5 |
| 396 | 5.0 | 8.0 | 3.0 | 6.0 |
| 400 | 6.0 | 7.5 | 5.0 | 3.0 |
| 416 | 5.5 | 8.0 | 6.0 | 2.5 |
| 423 | 3.5 | 7.5 | 3.5 | 2.0 |
| 442 | 5.5 | 7.5 | 4.5 | 1.0 |
| 451 | 6.5 | 7.5 | 5.0 | 2.5 |
| 452 | 5.5 | 8.0 | 5.0 | 3.0 |
| 453 | 5.5 | 8.0 | 3.0 | 1.0 |
| 454 | 6.0 | 8.0 | 5.5 | 2.0 |
| 455 | 5.5 | 8.0 | 4.0 | 1.0 |
| 456 | 5.5 | 8.0 | 6.5 | 2.5 |
| 457 | 7.0 | 7.5 | 6.5 | 1.0 |
| 458 | 4.5 | 7.5 | 2.0 | 5.5 |
| 459 | 5.0 | 8.0 | 3.0 | 1.0 |
| 460 | 5.5 | 8.0 | 5.5 | 1.5 |
| 461 | 6.0 | 8.0 | 7.0 | 3.5 |
| 462 | 5.5 | 7.5 | 4.0 | 1.0 |
| 463 | 5.5 | 5.5 | 3.5 | 1.0 |
| 464 | 5.5 | 8.0 | 5.0 | 4.0 |
| 466 | 5.0 | 8.0 | 4.5 | 2.0 |
| 468 | 4.5 | 6.5 | 5.5 | 1.0 |
| 469 | 5.5 | 8.0 | 4.5 | 1.5 |
| 475 | 5.5 | 8.0 | 4.0 | 3.0 |
| 477 | 6.5 | 7.5 | 5.5 | 1.5 |
| 478 | 5.5 | 8.0 | 5.0 | 2.0 |
| 480 | 6.5 | 8.0 | 6.0 | 2.5 |
| 482 | 6.5 | 7.5 | 6.5 | 2.5 |
| 483 | 5.5 | 8.0 | 5.0 | 1.5 |
| 484 | 5.0 | 8.0 | 4.0 | 1.0 |
| 485 | 6.0 | 8.0 | 2.0 | 2.0 |
| 487 | 5.5 | 8.0 | 4.5 | 2.0 |
| 488 | 6.0 | 3.5 | 5.0 | 2.5 |
| 489 | 7.0 | 8.0 | 5.5 | 2.5 |
| Tift 94 | 7.0 | 8.0 | 2.5 | 2.0 |
| Tifdwarf | 5.5 | 5.5 | 1.5 | 8.5 |
| Tifgreen | 6.0 | 7.5 | 2.0 | 8.0 |
| TifEagle | 7.0 | 7.0 | 1.0 | 4.5 |
| Range | 2–8 | 3–9 | 1–7 | 1–9 |
| Anova | | | | |
| Entry | .0035 | .0001 | .0001 | .0001 |
| Rep | .0039 | .0636 | .0279 | .5678 |
| CV | 1712 | 812 | 2512 | 3312 |
| 5% LSD | 1.9 | 1.1 | 2.0 | 1.8 |

| Mole Cricket Damage | | Mole cricket damage | Green up |
|---|---|---|---|
| Entry | 8/2 | 1 = none | 1 = poor |
| Tift94 | 2.5 | 9 = susceptible | 9 = best |
| Tifdwarf | 6.5 | | |
| Tifgreen | 6.0 | Color | Seed Heading |
| TifEagle | 3.5 | 1 = brown | 1 = no heads |
| 355 | 4.5 | 9 = dark green | 9 = complete |
| range | 2–8 | | heads exserted |
| Anova | | | |

TABLE 16-continued 1996 greenup, color, % seed heads and mole cricket damage ratings on dwarf bermudagrass selections in 1995 Greens Test planted 4-7-95. (tifdwf96)

| | |
|---|---|
| Entry | .1826 |
| Rep | .4320 |
| CV | 32 |
| 5% LSD | 4.0 |

4/7/96 - T557, T568, T589 are susceptible to mole cricket damage both reps rated three.

Note:

Test consisted of 2.4 m × 2.4 m plots and two replications mowed at 6 mm.

TABLE 17

Ratings for number of seed heads on turf bermudagrass on 6-11-96 (A1994, A1995, I1995, I1991)

| | Test | | Increase | |
|---|---|---|---|---|
| | 1994 | 1995 | 1995 | 1991 |
| TifEagle | 1.0 | 1.0 | 1.0 | 1.0 |
| Tifgreen | 2.5 | 3.0 | | 5.8 |
| Tifdwarf | 3.5 | 5.5 | 4.3 | 6.5 |
| #355 | | 1.0 | | |
| Anova: | | | | |
| Rep | .1835 | .3910 | .5000 | .9306 |
| Entry | .0500 | .0027 | .0141 | .0001 |
| CV | 17 | 13 | 34 | 17 |
| 5% LSD | 1.7 | 1.1 | 2.0 | 1.3 |

Ratings:

1 = None

9 = 100% Heading

Note:

1994 and 1995 test each consisted of two replications. Four random ratings were made on the 1991 and 1995 increase plots (10 m × 10 m).

TABLE 18

Turf quality ratings on Tifdwarf and TifEagle bermudagrass mowed at 3(*), 4(), or 5(*) mm.

| | Turf Quality | | | | |
|---|---|---|---|---|---|
| | The Landings - Savannah, GA | | West Palm Beach Banyan | Hobe Sound, FL Jupiter Island | Overall |
| | Oakridge(*)[1] | Marshwood(*)[2] | GC(**)[3] | GC(***)[4] | Mean |
| Tif-dwarf | 5.2 | 6.0 | 4.3 | 7.5 ± 0.5 | 5.4 |
| Tif-Eagle | 8.6 | 8.5 | 7.5 | 9.0 = 0.5 | 8.3 |
| | 0.005 | 0.005 | 0.007 | | 0.0001 |

[1]Established practice green on 7-1-84. Mean of 1995 and 1996 ratings.
[2]Established nursery green on 5-4-94. Mean of 1995 ratings.
[3]Established practice green on 3-14-94. Mean of 1995 and 1996 ratings.
[4]Established practice green on 9-15-95. Mean of 1996 ratings (one rating) (Mean ± SE).
Ratings: 1 = poor, 9 = best.

TABLE 19

Mean turf ratings of Tifdwarf, Tifgreen and TifEagle bermudagrass mowed at 3(*), approximately 4() and 5(*) mm height.

| | Pinehurst, NC *4 Course(***)[1] | | Ft. Lauderdale, FL (**)[2] | | Memphis, TN |
|---|---|---|---|---|---|
| | Density | Quality | 1995 | 1996 | Memphis CC(*)[3] |
| Tifdwarf | 7.5 | 7.0 | 6.3 | 6.9 | 4.0 ± 1.0 |
| TifEagle | 8.0 | 8.0 | 8.3 | 8.0 | 8.0 ± 0.0 |
| 5% LSD | 1.5 | 0.8 | 2.1 | 0.6 | |

[1]Planted nursery green on 6-28-93. Mean of 1994 and 1995.
[2]Planted plots in 1993. 1995 is mean of year. 1996 is June 20.
[3]Planted 5-13-96. 1996 ratings. Mean ± SE. Control cultivar is Tifgreen.
Ratings:
1 = poor,
9 = best.

TABLE 20

Rating (9-30-96) on bermudagrass turf established on 5-13-96 at Memphis Country Club. (Memp96)

| Entry | Density | Color |
|---|---|---|
| Tifgreen | 3.5 + 1.5 | 5.5 + 0.5 |
| TifEagle | 7.5 + 0.5 | 9.0 + 0.0 |

Notes:
A)1 = poor, open or brown and 9 = best, dense or dark green for quality, density and color, respectively.
B) Test mowed at 3 mm daily
C) At least ⅔ of the green has heavy shade in the AM. Algae was dense in the shaded area of Tifgreen but none was observed in TW72.
D) Rated with Carl Murphree (Rodney Lingle - Superintendent)
E) one-half of practice green was planted to each TifEagle and Tifgreen.

TABLE 21

Mean ratings for color and stimp on Turf Bermudagrass on various golf courses[1]

| | COLOR Marshwood (The Landings) (Savannah, GA) 2 | | | STIMP (feet) Oakridge (The Landings) (Savannah, GA) 3 | | |
|---|---|---|---|---|---|---|
| | 9 Mar 95 | 9 Oct 95 | x | 9 Oct 95 | 27 Aug 96 | x |
| TifEagle | 4.0 | 5.0 | 4.5 | 8.1 | 8.3 | 8.2 |
| Tifdwarf | 2.5 | 3.0 | 2.8 | 7.2 | 7.8 | 7.6 |
| t-test for significance | | 0.006 | | | 0.04 | |

[1]Data was analysed across dates as paired comparison using a 't' test for significance.
[2]Mowed at 3 mm. Green establiohed 5-4-94. Superintendents Ralph Hinz and Alan Young.
[3]Mowed at 3 mm. Green established 7-1-94. Superintendents Ralph Hinz and Bobby Sisk.
Note:
Color: 1 = brown, 5 = green. All greens had two random 6 m × 6 m blocks of Tifdwarf as a control. Ratings at each date consisted of a rating on each Tifdwarf block and two random ratings on TifEagle.

TABLE 22

Measurements on 5 cm diameter × 6 cm deep plugs on June 3, 1997 taken from unmowed plots planted as single rooted plants from 5 cm pots on April 10, 1997[1]

| Entry | Green root plus shoot wt. (g) | No. shoots per 1963 mm$^2$ | Shoot length (mm) | Leaf length (mm) | Leaf width (mm) |
|---|---|---|---|---|---|
| Tifdwarf | 7.24 | 103 | 22.5 | 13.4 | 1.28 |
| TifEagle | 8.65 | 129 | 17.8 | 10.2 | 1.14 |
| Flora-dwarf | 5.01 | 115 | 17.7 | 7.5 | 1.23 |
| LSD (0.05) | 2.29 | 20 | 2.2 | 1.4 | 0.13 |

| | Internode length | | |
|---|---|---|---|
| Entry | 1 | 2 | 3 |
| Tifdwarf | 13.2 | 12.5 | 11.8 |
| TifEagle | 10.5 | 11.1 | 10.3 |
| Flora-dwarf | 9.5 | 9.7 | 10.2 |
| LSD (0.05) | 1.4 | 1.6 | 1.5 |

[1]Ten replications

TABLE 23

Measurements on 5 cm diameter × 6 cm deep plugs on June 3, 1997 taken from plots established May 10, 1996 and mowed at 6 mm[1]

| Entry | Green weight of roots plus shoots (g) | Number of shoots per 1963 mm$^2$ |
|---|---|---|
| Tifdwarf | 15.94 | 137 |
| TifEagle | 14.15 | 180 |
| Floradwarf | 14.67 | 189 |
| Champion | 13.28 | 188 |
| LSD (0.05) | 2.93 | 33 |

[1]Five replications

What is claimed:

1. A new and distinct cultivar of bermudagrass plant, substantially as herein shown and described, distinguished by shorter shoot and leaf length, narrower leaves, more shoots per unit area, production of high quality turf when mowed at less than 6 mm height, improved tawny mole cricket resistance after the year of establishment and a distinct DNA pattern(s) measured by the fluorescent-labeled AFLP method.

* * * * *